United States Patent
Rath et al.

(10) Patent No.: US 9,101,334 B2
(45) Date of Patent: Aug. 11, 2015

(54) METHOD AND SYSTEM FOR REAL TIME VISUALIZATION OF INDIVIDUAL HEALTH CONDITION ON A MOBILE DEVICE

(71) Applicants: Matthias W Rath, Aptos, CA (US); Aleksandra Niedzwiecki, Aptos, CA (US); Dirk Fried Karnath, Duesseldorf (DE)

(72) Inventors: Matthias W Rath, Aptos, CA (US); Aleksandra Niedzwiecki, Aptos, CA (US); Dirk Fried Karnath, Duesseldorf (DE)

(73) Assignee: Matthias W. Rath, Aptos, CA (US)

( * ) Notice: Subject to any disclaimer, the term of this patent is extended or adjusted under 35 U.S.C. 154(b) by 0 days.

(21) Appl. No.: 14/613,506

(22) Filed: Feb. 4, 2015

(65) Prior Publication Data
US 2015/0149217 A1 May 28, 2015

Related U.S. Application Data

(63) Continuation-in-part of application No. 13/209,382, filed on Aug. 13, 2011, now Pat. No. 8,968,004, and a continuation-in-part of application No. PCT/US2013/023200, filed on Jan. 25, 2013, and a continuation-in-part of application No. 13/525,499, filed on Jun. 18, 2012.

(51) Int. Cl.
*G06F 3/01* (2006.01)
*A61B 5/00* (2006.01)
*G06F 19/00* (2011.01)

(52) U.S. Cl.
CPC .............. *A61B 5/7435* (2013.01); *A61B 5/0022* (2013.01); *A61B 5/4833* (2013.01); *A61B 5/7264* (2013.01); *G06F 19/322* (2013.01); *G06F 19/3406* (2013.01)

(58) Field of Classification Search
USPC ......................................................... 434/262
See application file for complete search history.

(56) References Cited

PUBLICATIONS

Mark Houston, The role of nutrition and nutraceutical supplements in the treatment of hypertension, World J Cardiol Feb. 26, 2014; 6(2): 38-66.
Klaus K. A. Witte et.al. Chronic Heart Failure and Micronutrients, Journal of the American College of Cardiology vol. 37, No. 7, 2001.
Blue cross blue shield document, Intracellular Micronutrient Analysis, Jul. 2014.
HMSA, Blue cross blue shield document, Intracellular Micronutrient Analysis, Nov. 1, 2013.

*Primary Examiner* — Kesha Frisby
(74) *Attorney, Agent, or Firm* — Geeta Kadambi; Riddhi IP LLC

(57) ABSTRACT

A method and technology to display 3D graphical output for a user using body sensor data, personal medical data in real time is disclosed. A consolidated methodology to bring user meaningful life information based on real-time sensor results, analysis, expert Q&As, "What if" scenarios and future emulation all in one artificial intelligence expert system is described. A unique rendering of 3D image of ones organ, cell or subcellular level display related to one's health condition can be visualized on a graphical user interface of a devices or devices. The change of the display from one level such as from organ to cell or cell to subcellular level or vice versa is enabled is disclosed.

10 Claims, 29 Drawing Sheets

METHOD AND SYSTEM FOR REAL TIME VISUALIZATION OF INDIVIDUAL HEALTH CONDITION ON A MOBILE DEVICE

CROSS REFERENCE TO RELATED APPLICATIONS

The instant application is a continuation in part of the U.S. application Ser. No. 13/209,382 filed on 13 Aug. 2011, now allowed and Ser. No. 13/525,499 filed on 18 Jun. 2012 and PCT application PCT/US13/23200 filed on 25 Jan. 2013. The pending U.S. Applications and the PCT applications are hereby incorporated by reference in its entireties for all of its teachings.

FIELD OF TECHNOLOGY

This disclosure relates generally to a field of a method and system for real time visualization of individual health condition on a mobile device. More particularly, it relates to a personal device used by an individual to observe and monitor their health condition during certain activities.

BACKGROUND

National health cost and personal insurance cost for health care has increased and continues to increase year after year. Personal health care monitoring becomes essential to keep these costs down for young and old people alike. There is a need for personalized devices that actually monitors ones health on a daily basis and keeps one fit.

Unattached sensors are available that can be carried by the person in pocket or handbag that measures certain vital parameters affecting general health. Unattached sensors have communication capability to relay these metrics over wireless or wired medium to the monitoring units.

A lot of wearables and personal devices enable users to monitor various physiological parameters such as fit bits, laser blood flowmeter, wireless blood pressure monitors, pulse oximeter, wrist watches with pulse readers, blood pressure cuff, exercise gadgets etc. Their input is disparate and does connect ones health to relevant data such as exercise, food and health.

There is need for an alternate format of integrated tool that may be suitable for all ages and several disciplines, demographics and stages for health monitoring and education.

SUMMARY

Several embodiments for a system and method for a real time visualization of the individual health condition on a mobile device or other devices are disclosed. In one embodiment, the mobile device would display a specific organ by gathering the vital signs, nutrition, activity level and medical data of a person who is wearing or using the device.

In one embodiment, a device displaying the image of the health condition may be used for visualization, monitoring, analyzing the health condition of a given individual in real time. The device display may be customized or added on to the existing devices as a screen to display the health condition.

In one embodiment, a user can participate in creating the input, study the content, share the content and interactively use the content. The user may also explore the image at an organ level, cross sectional view and at a tissue level. In another embodiment, the user may interactively observe, change and learn effect of modulation of at least one of micronutrients, drugs, environmental toxins and pathogen levels and their effect on cellular level, organ level and tissue level. Micronutrients may be, not limited to, vitamins, amino acids, supplements; drugs may be chemotherapy drugs, antibiotics, antihistamines, steroids etc.

In another embodiment, the user can understand the different functionality of micronutrients affecting the microenvironment of the cells and their effects of modulation in the cell and their general health.

In one embodiment, the system may be able to receive and interact with various other devices, sensors, wearables, monitors, databases, wireless connected devices, data and manual input and to collate the data and display a rendition of an organ and its sub parts in real time. The data when received and transmitted will comply with local authority rules such as HIPPA compliance.

The system in one embodiment may have many modules that have different functions to integrate the individual data and present the image of the organ. The rendering of the image, in another embodiment, may be the result of cause and effect that depends on the input, activity and nutritional status along with the medical status of the individual.

In one embodiment, a system may comprise of various mobile devices and devices such as tablets, wrist band devices, iPad, computers, cell phones, gaming devices, chairs, vehicle portals and wearables such as, but not limited to, a watch or eye glasses. The data may be portable from one device to another. All the devices may be connected using a network, and the data may be stored in a database or a cloud based storage arrangement.

The system comprises of several modules, and all of them are run on hardware's. In one embodiment, a processor may contain a user module, device module and a server module. In another embodiment, a method of gathering at least one of a physiological parameter, pathological parameter and therapeutic parameter automatically from a user to present for a personalized interactive display for the user on a mobile device. In another embodiment, rendering of at least one of a personalized reformatable physiological model and pathological model at the level of an organ, a cross section of an organ, parts of an organ is done at the cellular level of an organ and the subcellular level of said organ on the device. The device may be mobile or wearable.

In another embodiment, switching from one level to another (e.g. organ to cell or cell to subcellular) on that visual device by performing a swiping action on a screen of the device. A reverse sweep also would render the image to revert to the previous state of display. In one embodiment, dynamically updating a relevant data pertaining to a normal, disease and treatment option; and recording a variable in the user health for a data storage purpose is done.

In one embodiment, modifying at least one of the physiological parameter, pathological parameter and therapeutic parameter on the screen of the device and changing the rendition of the organ and the cellular level to show the effect is performed.

In one embodiment, body sensors constituting implanted sensors, mini robotic sensors that may circulate in the body, surface mounted sensors and accompanied unattached sensors communicate over wireless medium to user devices consisting of tablet, laptop, desktop and smart device to collect important physiological information to be stored in local database and track the information through proper metrics.

In one embodiment, user devices obtaining important sensor information and storing in local data base provide access to and manage the information through a methodology that include graphical user interface.

In one embodiment, App intelligence methodology in user devices access sensor data from local data base to analyze and display important physiological, health and body related information through graphical medium over display. In one embodiment, user device App intelligence consists of a methodology to communicate with cloud based expert system to bring important information on "What if" scenarios.

In one embodiment, user devices communicate body sensor information to the cloud based expert system in the back end that can exist anywhere in the world and not necessarily coexist with the user devices. In another embodiment, cloud based expert system collects sensor data, analyzes, computes, modifies and concludes based on past and present data.

In one embodiment, sensor data sent by user devices are stored in redundant user knowledgebase providing fault tolerance and enhanced reliability towards accessing and storing important user information.

In one embodiment, cloud based expert system stores educational knowledge in redundant education knowledgebase for experts and expert system methodology can tap into based on its artificial intelligence schema and provide accurate educational information to the user in user devices.

In one embodiment, education information is stored and managed using redundant education knowledgebase to enhance reliability. In one embodiment, experts access expert system through expert client interface to gather, analyze and advice in real-time users queries based on past and present sensor data In one embodiment, expert system artificial intelligence module analyzes "What if" scenarios based on hysteresis of past and present sensor data and using the expert system knowledgebase.

In one embodiment, cloud based expert system provides real time emulation of scenarios and displays through graphical and animation medium directly into user devices. In one embodiment, cloud based expert system directly accesses some of body sensors to initialize, set, get and reset values. In one embodiment, user interfaces in user device provides specific user based authentication so that user information is protected.

In one embodiment, user based authentication is provided for expert system, so that patient or user information access is protected.

The system consists of several modules that provide seamless collection of body sensor data over wired, wireless or cellular communication medium, not exclusive to standards such as WiFi, WiMAX, Cellular GSM, CDMA, Bluetooth and RFID to be stored in local storage medium and cloud based redundant storage servers. In one embodiment, user device App graphical interface provides a method to display sensor information, "What if" scenario emulation and an interface to dialog important questions to experts in back end.

The system consists of several modules that provide communication methodology between body sensors and user devices, body sensors and cloud based expert system, and user devices and cloud based expert system. The system consists of user device intelligence that collects sensor information, store and analyze the sensor information and display metrics set by the user real-time and ongoing basis. The user device intelligence also communicates with cloud based expert system to bring in the analyzed results and answers from experts to be displayed in the user device screen in proper format.

The methods and systems disclosed herein may be implemented in any means for achieving various aspects, and may be executed in a form of a machine-readable medium embodying a set of instructions that, when executed by a machine, cause the machine to perform any of the operations disclosed herein. Other features will be apparent from the accompanying drawings and from the detailed description that follows.

BRIEF DESCRIPTION OF THE DRAWINGS

Example embodiments are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

Several method, process and systems for informational, integrated and interactive educational modules using modular multimedia tools for medical, physiological and pathological conditions of the virtual human body are disclosed. This disclosure also relates to a comprehensive methodology of providing users a meaningful analysis of health based on sensor results by experts through analysis and emulation. More particularly, it relates to an artificial intelligence based expert system that continuously over real-time observes the sensor results, analyze through hysteresis and draws conclusion using experts and to meaningfully convey the health condition and education to the users.

Although the present embodiments have been described with reference to specific example embodiments, it will be evident that various modifications and changes may be made to these embodiments without departing from the broader spirit and scope of the various embodiments.

Figure 1:
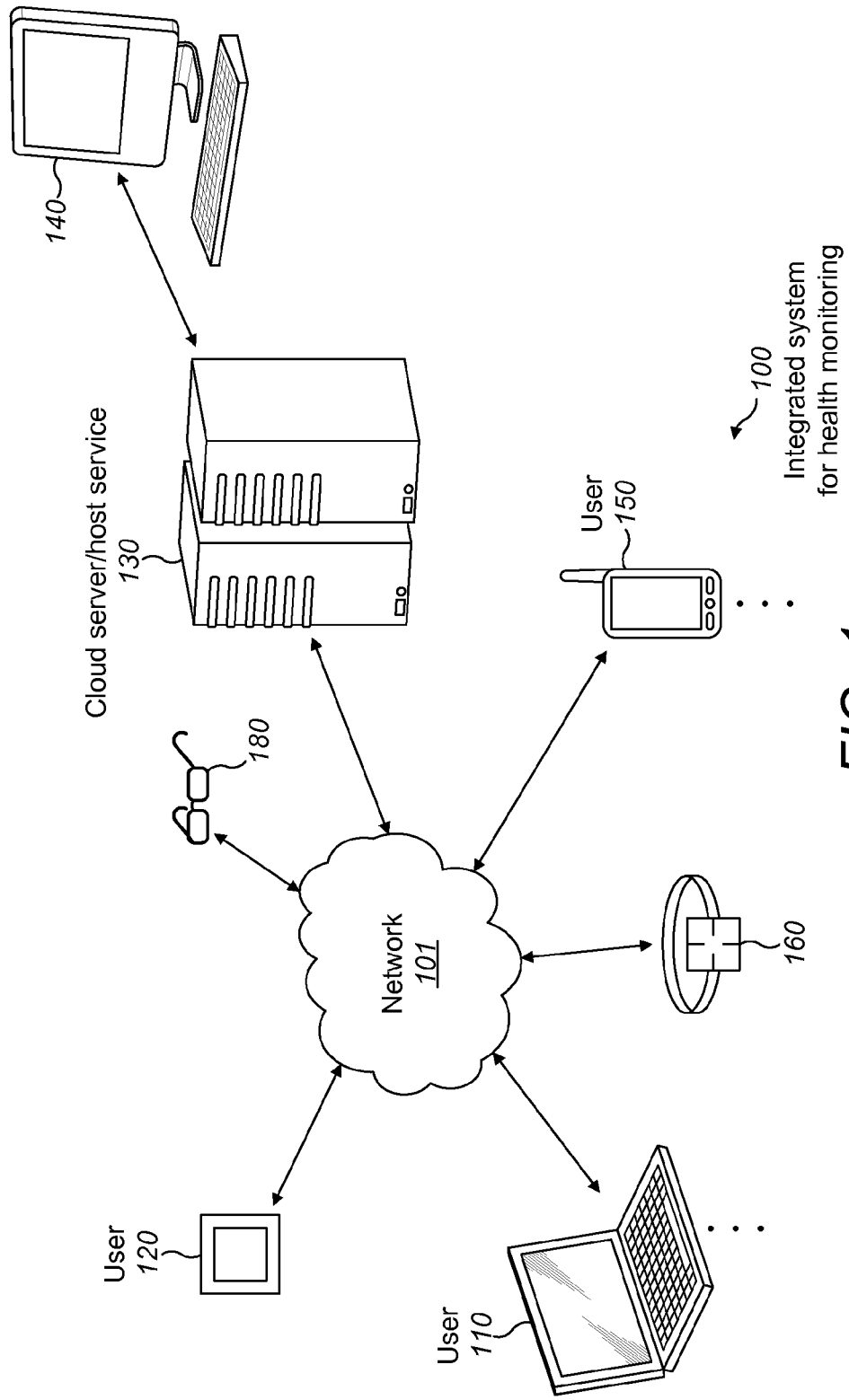
FIG. 1 is a systematic view of an integrated system for health monitoring 100 illustrating communication between user and the server through a network, according to one embodiment.

FIG. 1 is a systematic view of an integrated system for health monitoring 100 illustrating communication between user and the server through a network, according to one embodiment. In one embodiment a user or multiple users may connect to the server 130 that hosts the system. In another embodiment, the user hard ware such as a PDA, iPAd®, tablet, wearable such as eye glasses, wrist watches, watches, computer or a mobile phone or any wireless device, or an electronic book (e-book) may be connected with each other or work independently to allow the user to visualize personalized health condition. The network 101 may be a LAN, WAN, mobile, telecommunications, internet, intranet, WiFi and/or ZigBee network, etc. The user/individual having devices 110, 120, 140, 150 and 160 and so on may be a doctor, an individual, a nurse, a student, but not limited to these group of folks only. The user and individual are used interchangeably and mean the same. The user may be any person who accesses the device for viewing, altering, inputting their medical data, exercise data, nutritional data and observing the display of the organ of choice for a particular disease state or normal state.

Monitoring has reached the next level due to advances in body sensors. Sensors with communication modules built as a single unit can communicate with each other and form body sensor network. The sensor dimensions have reached a value where it can be easily implanted into the body. Implanted sensors have network connectivity where it can transfer data directly over wireless medium to the monitoring units. Surface mounted sensors are available that are worn in person that constantly monitor vital body information. The sensors have the capability to transfer information over wired or wireless medium to the monitoring units.

There is also a need for constant monitoring of information by experts and individuals who wear the sensors can consult an expert based on a measured event by sensors. Similarly, experts such as health care professionals can monitor their patients and intervene based on the measurements. There is a need for experts to analyze through hysteresis and come to important conclusions towards making a sound decision based on historical and present values collected through body sensor network.

There is a need for experts and the users to run "What if" scenarios based on past and present collected information and analyze the future to take important decisions towards introducing positive life changing activities.

Figure 2:
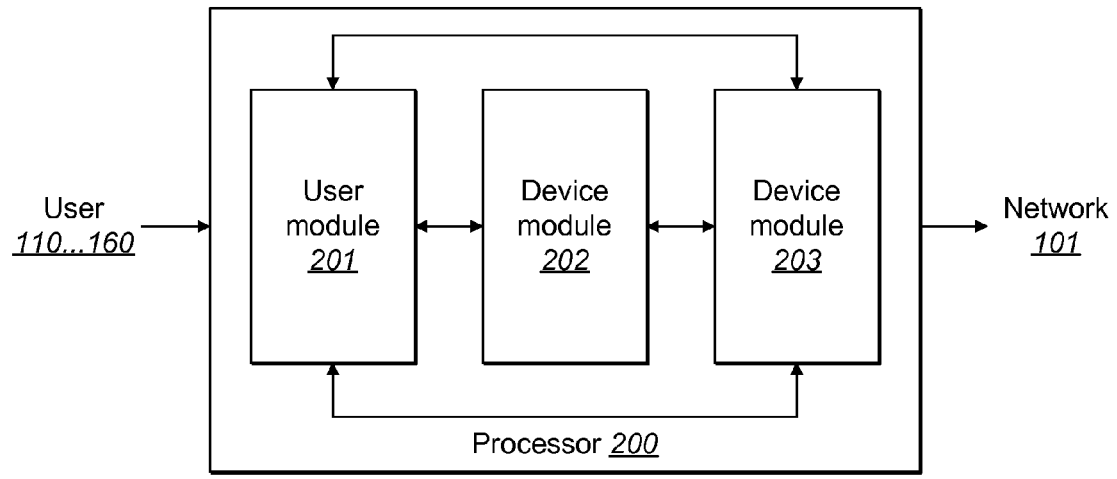
FIG. 2 illustrates an exploded view of the processor 200 containing different modules for the integrated system for health monitoring 100, according to one embodiment.

FIG. 2 illustrates, a processor 200 that may communicate to a user 110-N through a network 101. The user may have several types of devices such as an electronic book 120, multimedia, a phone 150, a computer 110 and 140, watch 160, wearable device, eye glasses 180, iPad, tablet, a PDA (Portable Digital Assistant), etc. Functions and components of the each module that is either housed or processed in a processor 200 or any other hard ware of choice, is discussed in the following paragraphs.

FIG. 2 also illustrates an exploded view of the user module 201, device module 202 and server module 203, according to one embodiment. All three modules interact with each other and share data to update the visual image that needs to be rendered when the method is started by the user. A virtual human organ or cellular level or subcellular level rendition may be created with all the details of each physiological system such as circulatory system, function of a cell, organ function such as a liver function, heart function, effect of nutrient deficiency in the heart or skin, effect of exercise or movement on the healthy heart, effect of nutrient sufficiency or deficiency on the normal, and diseased heart. The device module 202 and server module 203 would create a virtual human body as soon as the user chooses where and what to enter using the graphical user interface. The animation of the virtual human body with narration may be switched on or off. The purpose of this invention is to educate the user and evaluate the user for their ability to understand scientific facts and scenarios in a graphical format in real time.

The human body may be visualized at tissue level, cross sectional level, system level and/or an organ level. The system level is at least one of circulatory system, respiratory system, digestive system, musculoskeletal system, endocrine system, integumentary system, immune system, lymphatic system, reproductive system, urinary system, vestibular system and nervous system. The organ level is at least one of a brain, amygdala, basal ganglia, brain stem, medulla, midbrain, pons, cerebellum, cerebral cortex, hypothalamus, limbic system, eye, pituitary, thyroid, parathyroids, ears, heart, lung, esophagus, thymus, pleura, adrenals, appendix, bladder, gallbladder, large intestine, small intestine, kidney, liver, pancreas, spleen, stomach, prostate, testes, ovaries, uterus, breasts, hips, legs and throat.

The diseases are at least one of autoimmune diseases, cancer types, communication disorders, cutaneous conditions, metabolic disorders, endocrine diseases, eye diseases and disorders, genetic disorders, infectious diseases, intestinal diseases, heart diseases (arrhythmia, arteriosclerosis and heart attack) and neurological disorders.

In one embodiment, the effect of micronutrient concentration increase in preventing plaque formation may be observed by the user who is travelling inside the virtual human artery. In another example the effect of a heart attack may be felt by the red blood shaped space ship as crushing effect and a jolt and/or narrowing of the artery. These are examples and the embodiments are not limited to these examples. An individual is a user, teacher, patient, software developer, system manager and not limited to these definitions.

Figure 3:
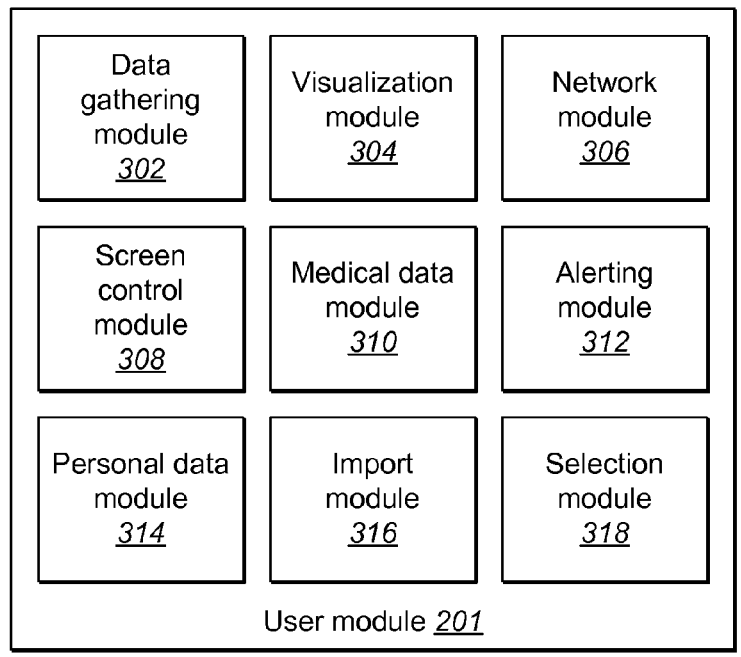
FIG. 3 illustrates an exploded view of a user module illustrated 201, according to one embodiment.

FIG. 3 illustrates an exploded view of a user module 201, according to one embodiment. In an embodiment, the user module 201 may include a data gathering module 302, a visualization module 304, a network module 306, a screen control module 308, and a medical data module 310, alerting module 312, personal data module 314, import module 316 and selection module 318.

The data gathering module 302 is used for getting medical data of the individual user, age, sex, weight, the nutritional information of what they ate, what nutritional supplements did they consume, what medications do they take, what type of exercise did they do and do on a regular basis, any other device that they use that collects vital signs, their projected goal such as a weight loss goal and a time limit for it. This module not only gathers data that has been input by the user into the device but also from other devices such as oximeter, fitbit, jawbone, sensors of other equipment's, blood pressure cuffs, heart rate monitoring devices etc. The data gathering module 302 interacts with import module 316 to get data from other equipment's that the user is using or attached to as a patient or an athlete. Network module 306 allows the user module 201 to communicate with other modules as well as other external equipment's for output of medical data and rendering the visual image of the organ after gathering the information from user module 201, device module 202 and server module 203 and allowing the processor to communicate with the user interface of the device.

Once the physiological parameter, pathological parameter and therapeutic parameter is collected and imported by import module 316 using the medical data module 310 and personal data module 314 the screen control module 308 helps the device to display an personalized interactive display of a particular organ is rendered at a cross sectional level, organ level and subcellular level. The screen control module 308 allows the user to switch from one level to another on the visual device by performing a swiping action on a screen of the device. The level change from one level to another level for example would be switching from organ to cell level and from cell to subcellular level and vice versa.

The visualization module 304 helps change the levels once the user decides to select a particular display using screen control module 308 and selecting the display with the help of the selection module 318. All these modules interact with each other to complete the function and as a result dynamically the image is updated using relevant data pertaining to a normal, disease and treatment option and recording the variable in the user health for a data storage purposes. Using the network module 306 the data may be stored in a data base cloud based server or host service 130 or a cloud based storage arrangement service.

Figure 4:
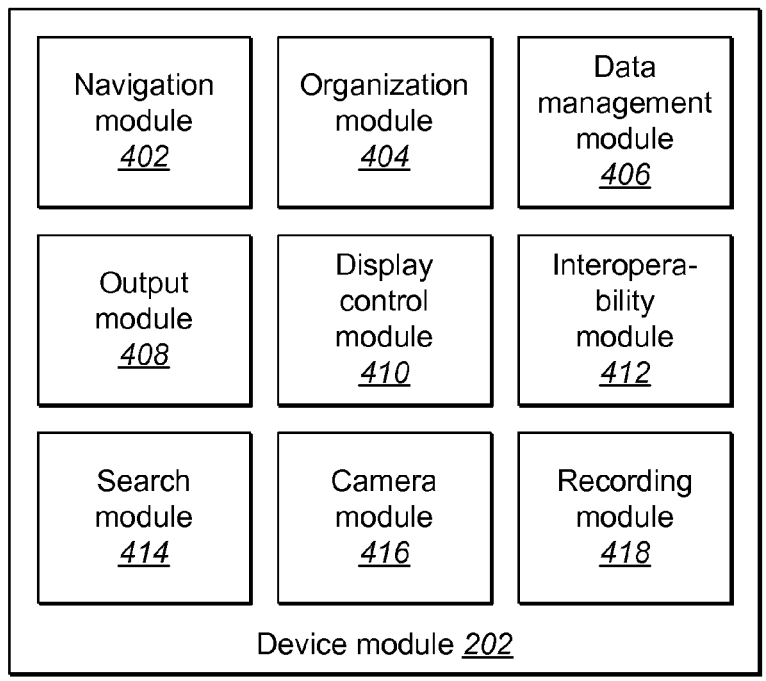
FIG. 4 is an exploded view of the device module 202, according to one embodiment.

FIG. 4 shows that device module 202 comprises of navigation module 402, organization module 404, data management module 406, output module 408, display control module 410, interoperability module 412, search module 414, camera module 416 and recording module 418. The data management module 406 gathers information from the user module and sort's relevant data that needs to be displayed and the solutions present for the given issue and passes it on to the organization module 404. Organization module 404 prioritizes the information gathered in pictorial form, text form, excel spread form, web based data form and from the database to display in graphical form and text form as suggestions.

Navigation module 402 is activated when the user touches the screen of the device and chooses a particular format, space or display to be offered to visualize in real time. For example the user may decide to see the cross sectional view of the heart to see the effect of running. Navigation module 402 allows the user to choose which format they want to see, how to go from one screen to another screen and save the results for future use. Display control module 410 works in conjunction with interoperability module 412 to display the user query in a uniform manner across all the devices that the user is using. For example if the cell phone has android operating system and his ipad® has another system it needs to enable the user to seamlessly import and export the data and display the image of choice. Search module 414 enables the user to search a particular nutrient or disease information for display. Camera module 416 allows the user to take a picture of a particular disease condition or an advertisement or a medical image such as x-ray and incorporate into the data management module 406 so it can be displayed with related and relevant data. Recording module 418 allows the user to record talks, seminars and comments or thoughts of the user and integrate into the display for future use.

Figure 5:
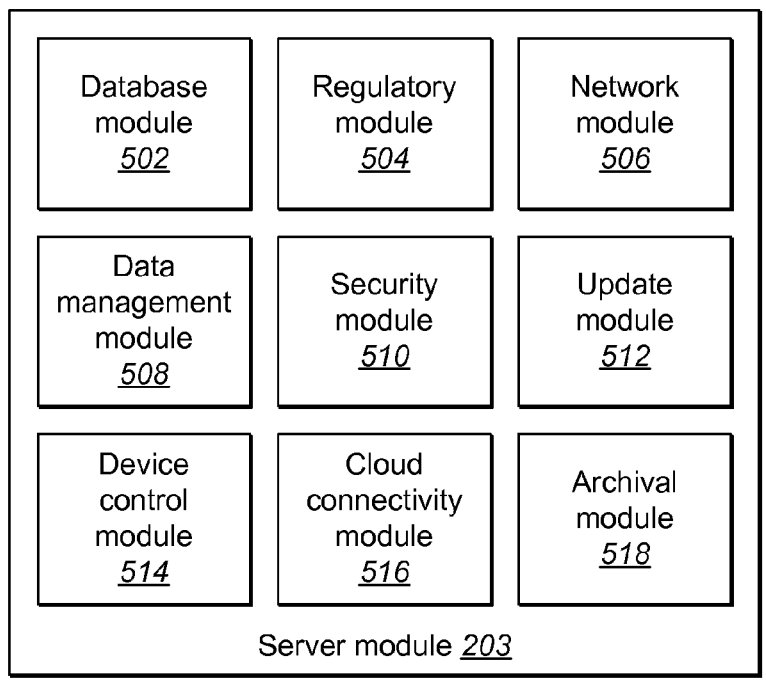
FIG. 5 is an exploded view of a server module 203, according to one embodiment.

FIG. 5 is an expanded view of the server module 203. The hardware functions along with the processor are controlled by this module. The database module 502 is different from other database module in several ways. It actually stores data and real time data is being extracted from this location and the network module 506 allows it to store in a remote location databases. Regulatory module 504 is an important module because it enables the data that is being used and obtained from different sources to be compliant with local authority rules such as HIPPA compliance, security compliance etc. Data management module 514 helps to process the regulatory rules compliant data to be processed and stored in proper format for real time use or future use. Security module 510 allows the device creator and the user to set a level of security to prevent medical data threat. It also helps prevent service provider that are not approved to get gain access for display or advertise their products and goods. Update module 512 enables the data to be current and any changes made by the user are instantly recorded in the database as well as display. Device control module 514 helps the developers and the device manufacturers to actually have control over the overall structural integrity of the operating system, display system and user capability rules. The user confirmation rules such as importing a irrelevant data into the device is controlled by this module. Permission setting for vendors is also done at this module level. With increasing data being produced and procured by the user the user may also choose to save their data in a cloud based storage space and cloud connectivity module 516 enables this function. Interoperability module 412 is also helped by this module using the network work module 506.

The archival module 518 is used for storing data that is being produced by the user in real time for further use. It may also be used by companies as big data for data mining purposes or historical perspective.

Figure 6:
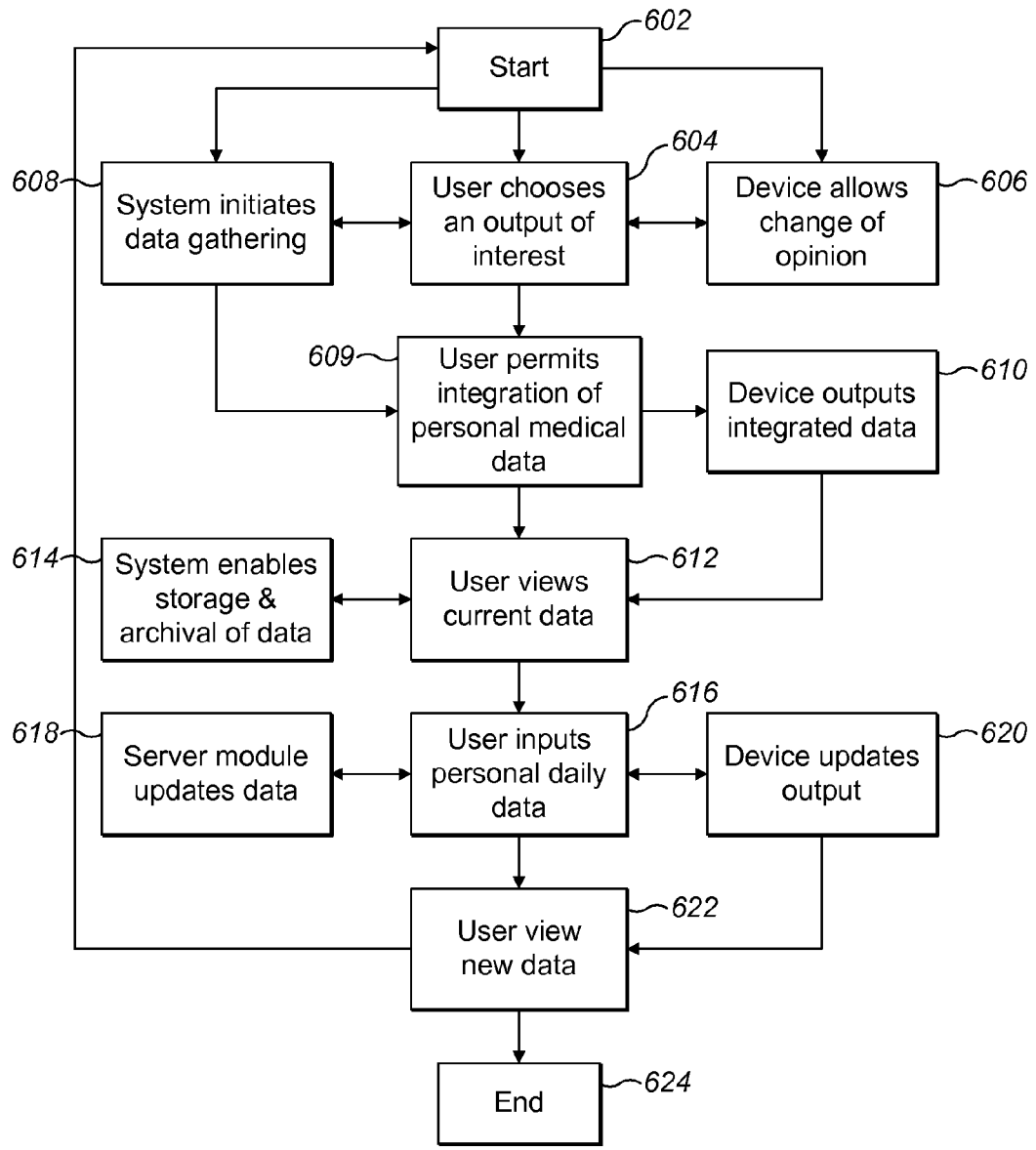
FIG. 6 is a flow chart of method of communication between different modules, according to one embodiment.

FIG. 6 is a method flow chart of the method being used. The steps may be added or deleted as the software matures and real time display requirements change. The user starts 602 the process by switching on the device. User may choose an output of interest 604 such as a heart function. System initiates data gathering 608 using different modules from user module 201, device module 202 and server module 203. Device on the interface level allows the change of option 606. The device may prompt the user to permit obtaining personal medical data for security purposes and the user has to permit integration of personal medical data 609. Once the data is gathered and integrated the device outputs integrated data 610. The user views the current data 612. The system enables the storage and archival of data 614 and this may be used for data mining or to offer suggestions at a later date. User may input his daily data or any change in personal data daily 616. The device integrates and updates output 620 and the user may view new data 622. Server module updates the change 618. All these modules work synchronously for a real time display of the image of choice. More about these functions and method flow will be discussed in detail with examples below. The process ends when the device is shut down 624. This work flow is just an example and there may be many more ways of using this device for real time display of personalized health condition of an individual.

Figure 7:
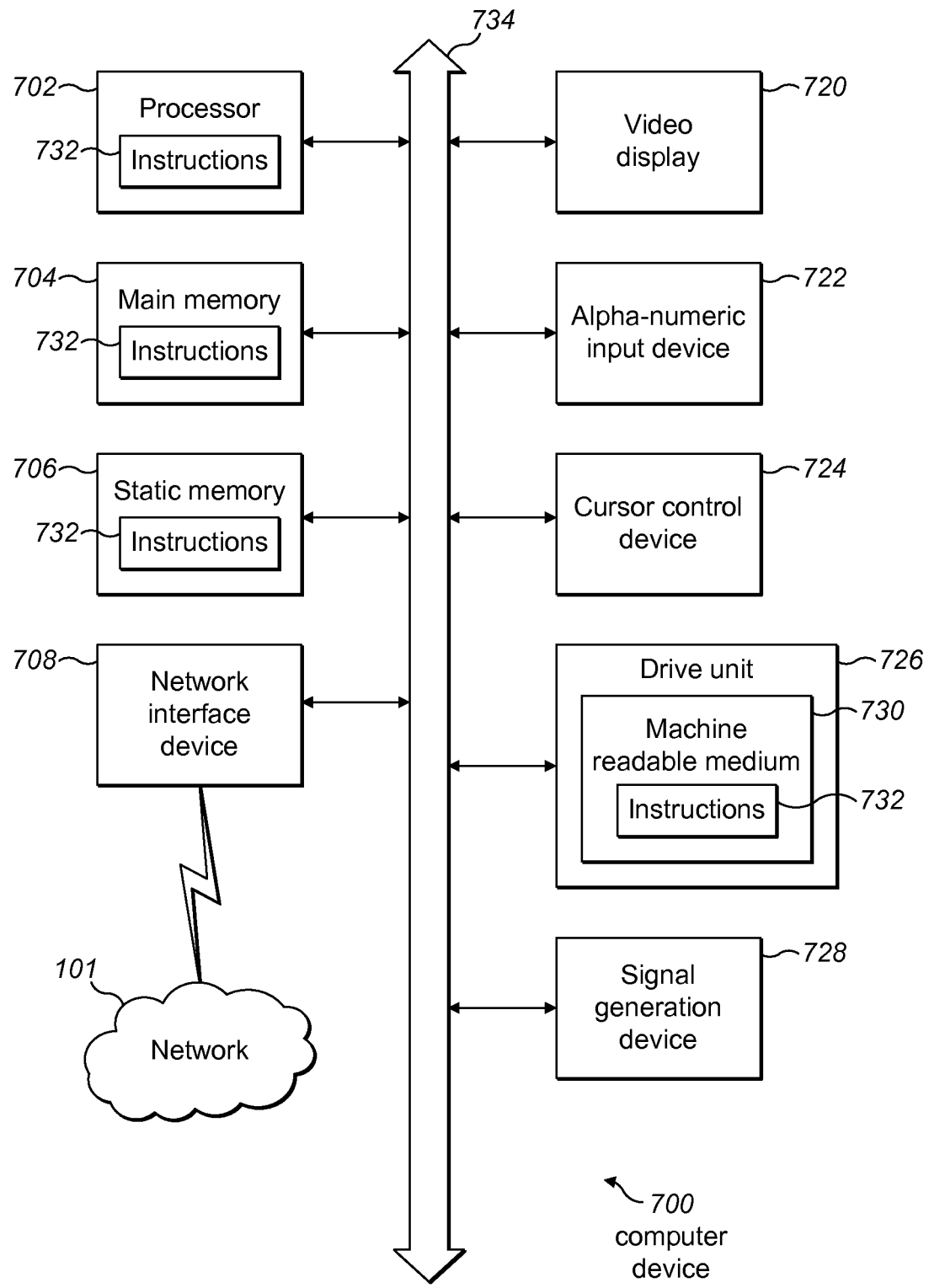
FIG. 7 is a diagrammatic system view of a computer device 700 view in which any of the embodiments disclosed herein may be performed, according to one embodiment.

FIG. 7 is a diagrammatic system view 700 of a computer device view in which any of the embodiments disclosed herein may be performed, according to one embodiment. Particularly, the computer system view 700 of FIG. 7 illustrates a processor 702, a main memory 704, a static memory 706, a bus 734, a video display 720, an alpha-numeric input device 722, a cursor control device 724, a drive unit 726, a signal generation device 728, a network interface device 708, a machine readable medium 730, instructions 732, and a network 101, according to one embodiment.

The computer system view 700 may indicate a personal computer and/or a data processing system (e.g., server) in which one or more operations disclosed herein are performed. The processor 702 may be microprocessor, a state machine, an application specific integrated circuit, a field programmable gate array, etc. The main memory 704 may be a dynamic random access memory and/or a primary memory of a computer system. The static memory 706 may be a hard drive, a flash drive, and/or other memory information associated with the computer system. The bus 734 may be an interconnection between various circuits and/or structures of the computer system. The video display 720 may provide graphical representation of information on the data processing system. The alpha-numeric input device 722 may be a keypad, keyboard and/or any other input device of text (e.g., a special device to aid the physically handicapped). The cursor control device 724 may be a pointing device such as a mouse.

The drive unit 726 may be a hard drive, a storage system, and/or other longer term storage subsystem. The signal generation device 728 may be a bios and/or a functional operating system of the data processing system. The network interface device 708 may be a device that may perform interface functions such as code conversion, protocol conversion and/or buffering required for communication to and from a network (e.g., the network 101 of FIG. 1). The machine readable medium 730 may provide instructions on which any of the methods disclosed herein may be performed. The instructions 732 may provide source code and/or data code to the processor 702 to enable any one/or more operations disclosed herein.

Figure 8:
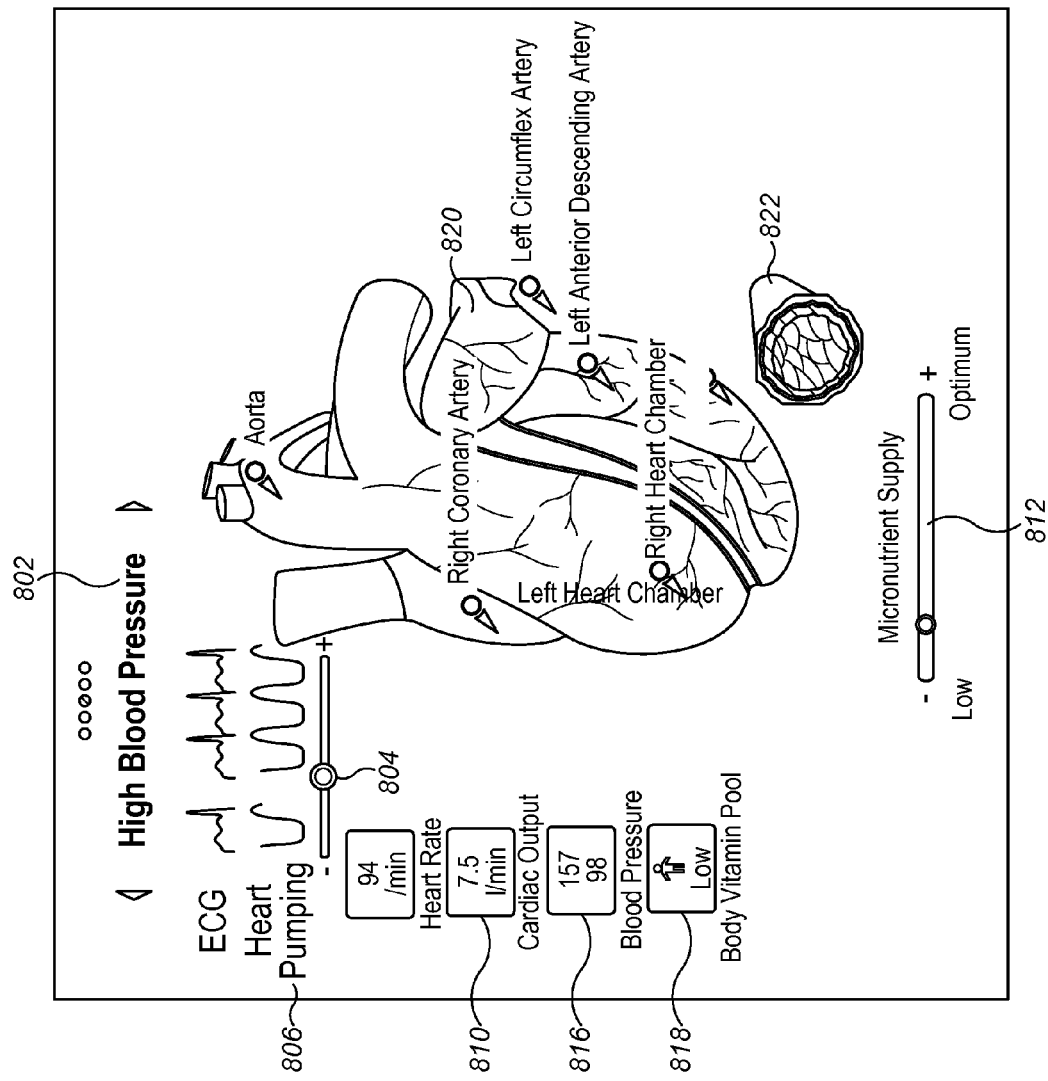
FIG. 8 is an example view of a high blood pressure model to show the effect of nutrient deficiency at an organ level, according to one embodiment.

FIG. 8 shows the display of the high blood pressure version of real time personalized graphic at the organ level. High blood pressure is a condition in which the force of the blood against your artery walls is high enough that it may eventually cause health problems, such as heart disease and it may be caused due to various factors including bad dietary habits. Prolonged high blood pressure leads to more complicated heart diseases such Arrhythmia, Arteriosclerosis, heart failure etc., but not just limited to these. Witte et. al. (2001) states nutrients, particularly vitamins C and E and beta-carotene, are antioxidants and may have a protective effect on the vasculature. High blood pressure generally develops over many years, and it affects nearly everyone eventually. Fortunately, high blood pressure can be easily detected. Everybody has busy life styles and do not have the time to read scholarly articles such as the review, books and research articles.

This invention simplifies the approach and integrates visual display, personal medical data, recommended macronutrient and micronutrient to maintain, treat and continue the treatment on a daily basis in real time. It enables people who are healthy to improve their healthy habits by keeping track of their physiology, nutrition, activity and diet in one integrated format. The visual display of the combined effect of daily factors provides a great impact for the user, medical students, researchers, nutritionist, physicians, sports person, children and elderly. Since it is personalized there is a great opportunity for service providers to automatically tailor the regiment of exercise or diet and see the beneficial effect of the said treatment and show it to the user. For children and adults it becomes an easy tool to convince that it is a good mode to keep in check and take care of oneself. Wearable mobile devices are the future and the instant invention makes it easier due to its portability and platform agnostic display and integration of personalized medical data.

FIG. 8 displays a simple rendition of the graphical display on the screen of the mobile device of a heart as an organ 820 that is real time and made specifically for the user. The figure also shows that an artery or a blood vessel 822 is also shown as a cross section. The mode 802 pertains to high blood pressure. The ECG and EKG data 806 is shown in real time. These data may be obtained from medical equipment's, sensors or any other format and integrated using interoperability module 412. The slide bar 808 basically allows the user to slide it up and down to see the effect of the increase in blood pressure and the change in parameters. Once the effect is shown the slide ruler comes back to the default state. The FIG. 8 also shows the numerical value of the cardiac output 816, blood pressure 816 and body vitamin pool 818. The body vitamin pool 818 shows different hues for deficiency, sufficient level and severely deficient level. The slider 812 shows micronutrient or a macronutrient or combinations thereof supply is at a low level if it is situated on the left side of the scale. The suggestions are made to improve the micronutrient pool automatically depending on the medical data that is obtained from the user and the correlate it to the medical data and the vital signs that are being recorded at that time.

Figure 9:
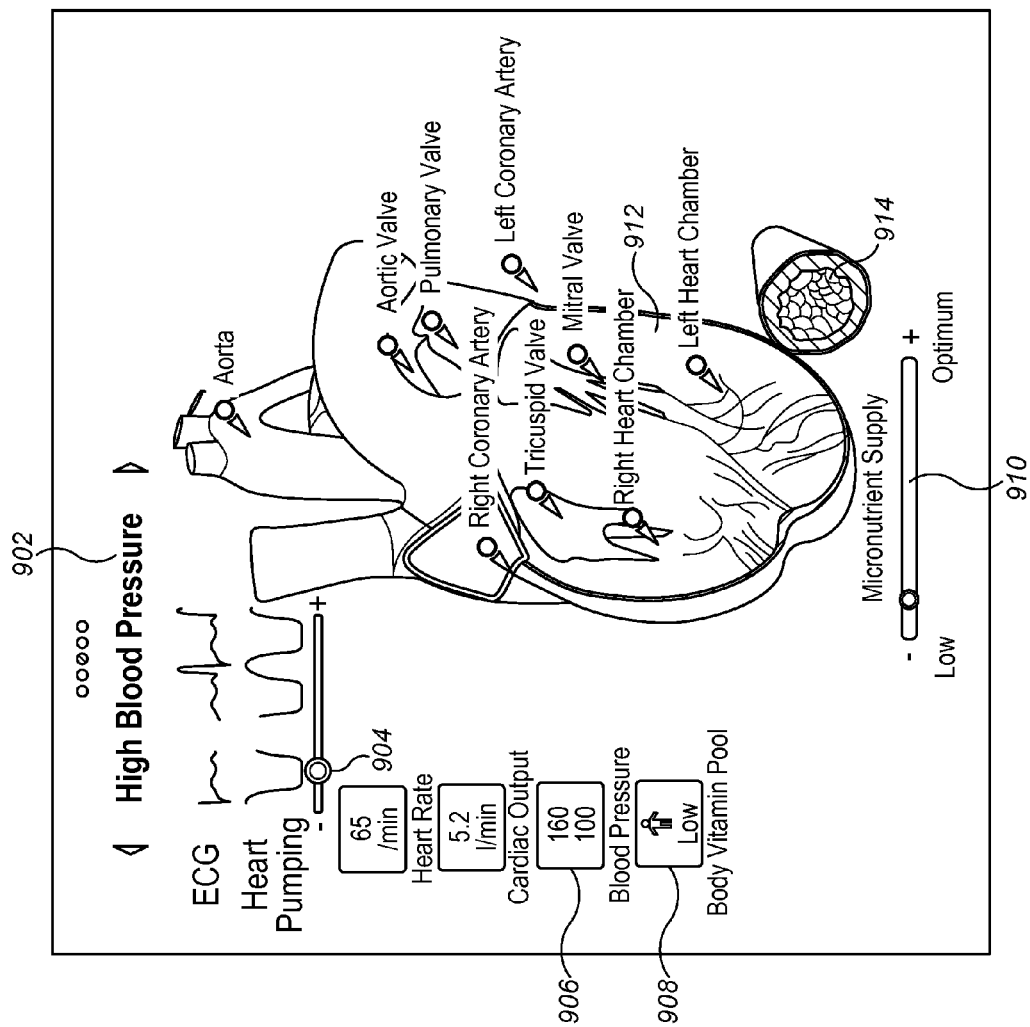
FIG. 9 is an example view of a high blood pressure model of heart and artery to show the effect of nutrient deficiency in a cross sectional heart, according to one embodiment.

The normal blood pressure is 120/80 mmHg. FIG. 9 shows the high blood pressure 902 at a different level. The slide bar 904, the blood pressure reading 906, and the body vitamin pool indicator 908 shows in red color as there is severe deficiency of the vitamin. The slide bar 910 also indicates the macronutrient or micronutrient level change effect. One very important disclosure in this figure is the artery 914 that shows the thickening of the walls and the interior of the heart 912 having thickening of the walls due to the deficiency of the vitamin pool or health condition. FIG. 9 also shows a cross section of the heart and shows lighting like lines to show short circuit spams of the heart muscle due to deficiency of the micronutrients. This type of visual display helps laymen understand the direct impact and the implication of good nutrition and when to take the supplements to prevent these disasters. There is a close correlation between diet and arterial disease as shown by Mark Houston (2014). Mark Houston (2014) states vascular biology, endothelial and vascular smooth muscle and cardiac dysfunction play a primary role in the initiation and perpetuation of hypertension and cardiovascular disease. Mark Houston (2014) also states that Macronutrients and micronutrients can prevent, control and treat hypertension through numerous mechanisms related to vascular biology. Decades of research conducted by Dr. Rath Research Institute also states and proves the same hypothesis and has products that are recommended by them. These products in various combinations may be displayed on the text section of each display that can be customized for each user.

Figure 10:
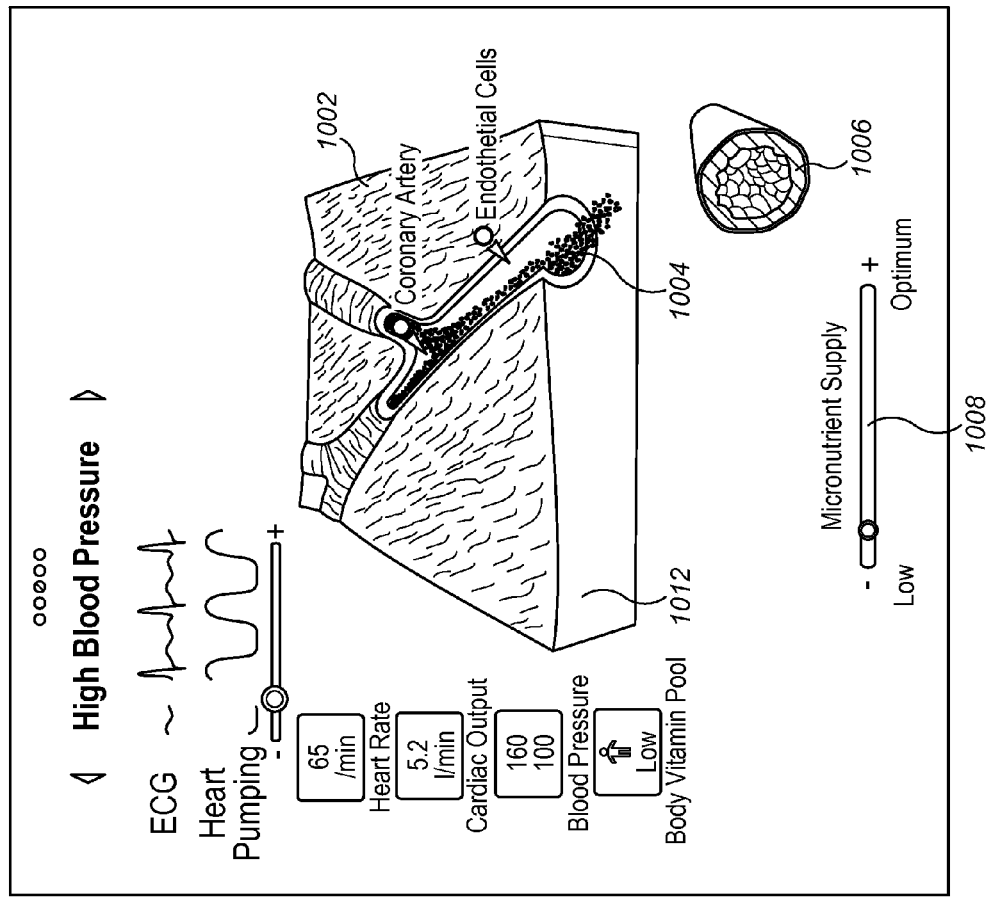
FIG. 10 is an example view of a high blood pressure model of heart tissue and artery to show the effect of nutrient deficiency in a cross sectional heart, according to one embodiment.

FIG. 10 shows tissue level graphical display of high blood pressure. The transition of the graphical user display can be achieved by a swiping action on the user interface and the organ such as a whole heart display will be changed to a cross sectional display and in one more swiping action will change over to tissue level display. The reverse may also be obtained by a swiping action on the screen of the device. FIG. 10 also displays the tissue 1012 and a cross section of the artery 1002 and micronutrients flowing in the artery 1004. It shows there is a deficiency in the volume of the micronutrients at this stage. The slide bar 1008 and arterial wall 1006 corroborates the fact with the slider 1008, the micronutrient flow 1004 and the high blood pressure readings. If the user wants to know what would happen if he takes micronutrients and slides the bar 1008 to the left then he would dynamically observe the change in the rendering of the heart tissue how it has improved. But if he keeps ignoring the alert sent by the alerting module 312 of the user module 201 the graphical rendition in real time will show that he might have a heart attack or severe breathlessness.

Figure 11:
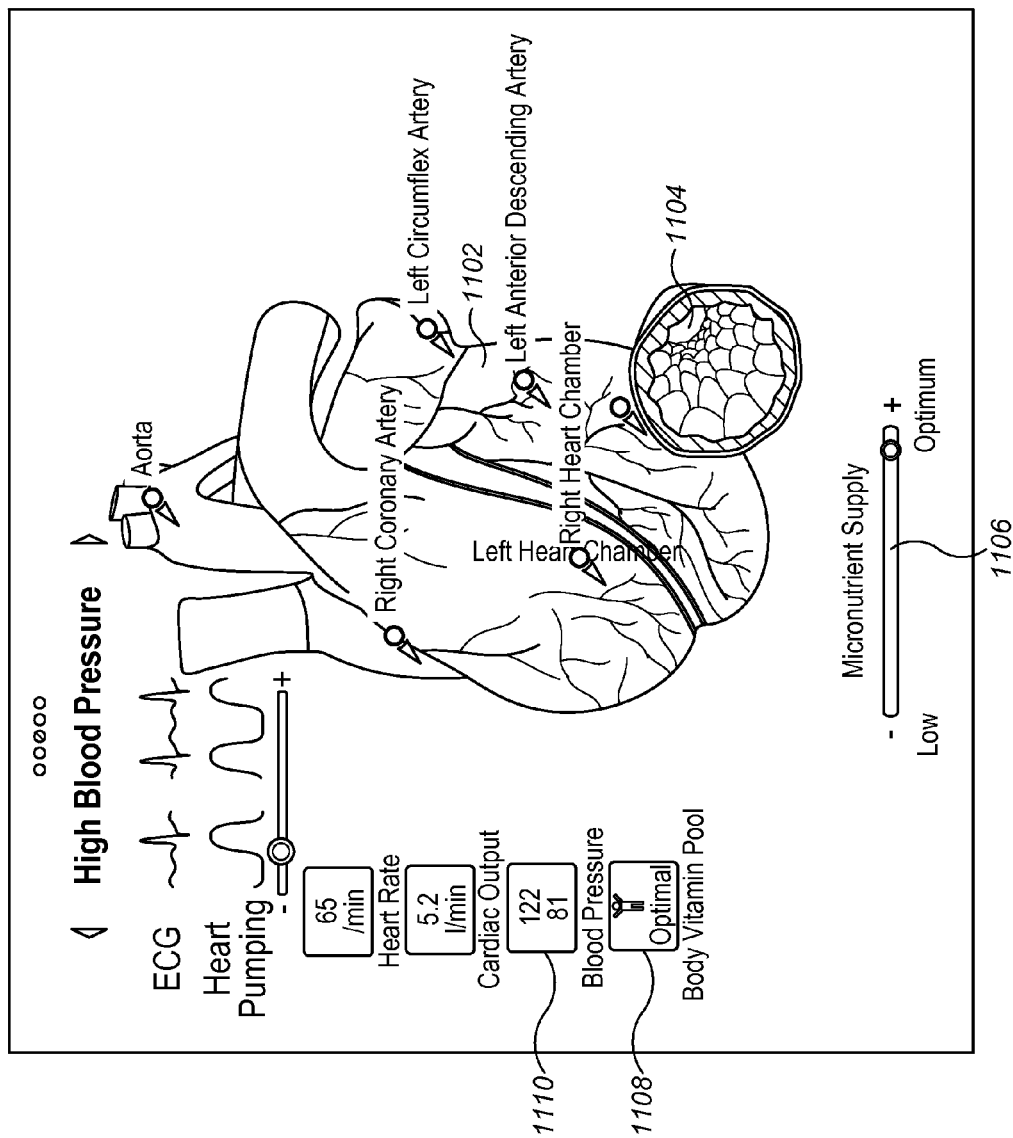
FIG. 11 is an example view of a high blood pressure model to show the effect of sufficient nutrient at an organ level, according to one embodiment.

FIG. 11 shows the organ heart 1102 when a user has high blood pressure condition and slides the micronutrient bar 1106 to the left the arterial wall thickness 1104 reduces, the blood pressure 1110 showing 122/81 compared to FIG. 9 and the vital signs such as blood pressure shows 160/100 and the body micronutrient pool 1108 shows a green color to show everything is in range. This would motivate the user to follow suggestions from the messages that may be sent to the user and continue to monitor their health to avoid chronic illness and sufferings.

Figure 12:
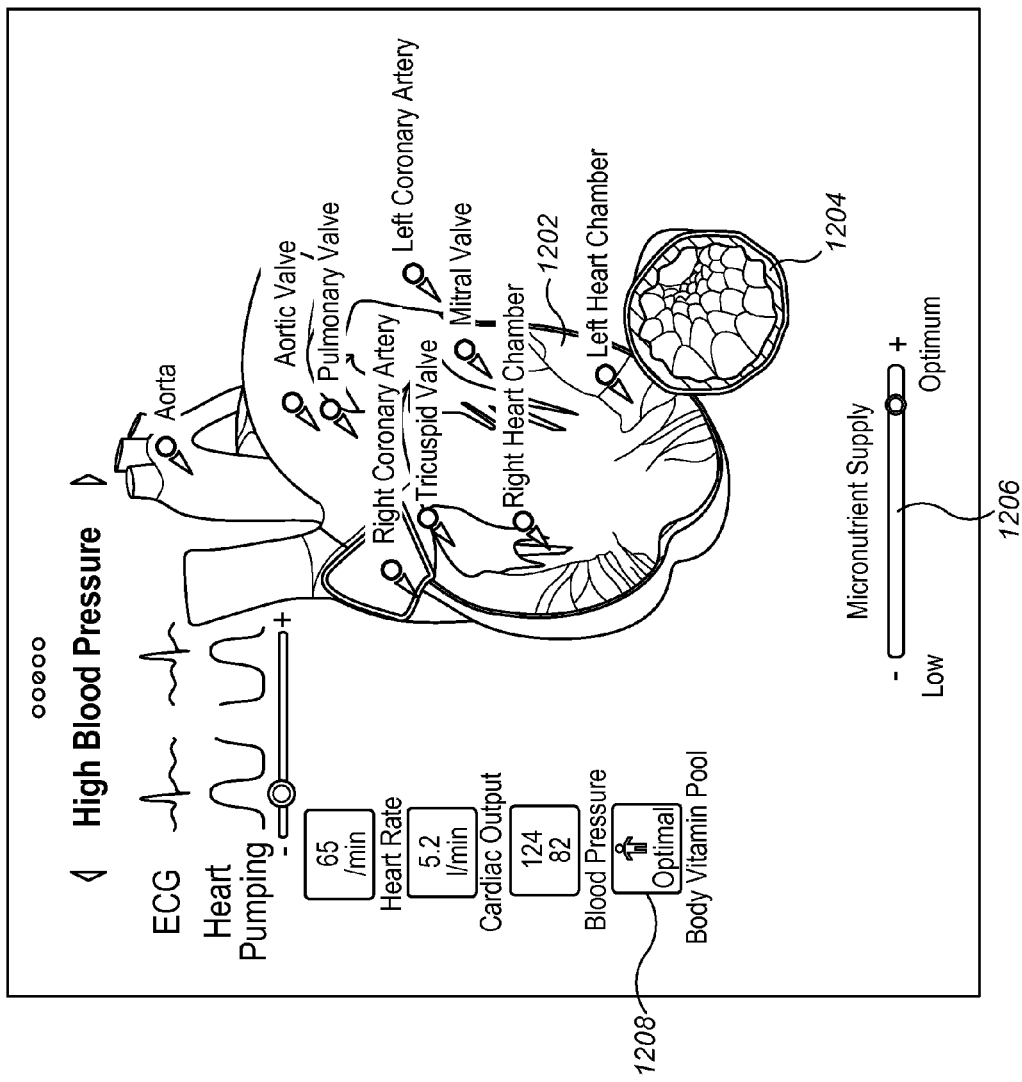
FIG. 12 is an example view of a high blood pressure model of heart and artery to show the effect of sufficient nutrient in a cross sectional heart, according to one embodiment.

FIG. 12 is a rendition of the same effect such as the FIG. 11 but a cross sectional view showing the sectional heart 1202. The arterial wall 1204 is also wide. The body vitamin pool 1208 is normal and shows green color. The cross sectional heart shows less amount of electrical impulses 1202 and the micronutrient/macronutrient supply bar 1206 is showing green and on the right side. The display may also allow monitoring of pharmaceutical drug therapies', 'pharmaceutical interventions' or alike.

Figure 13:
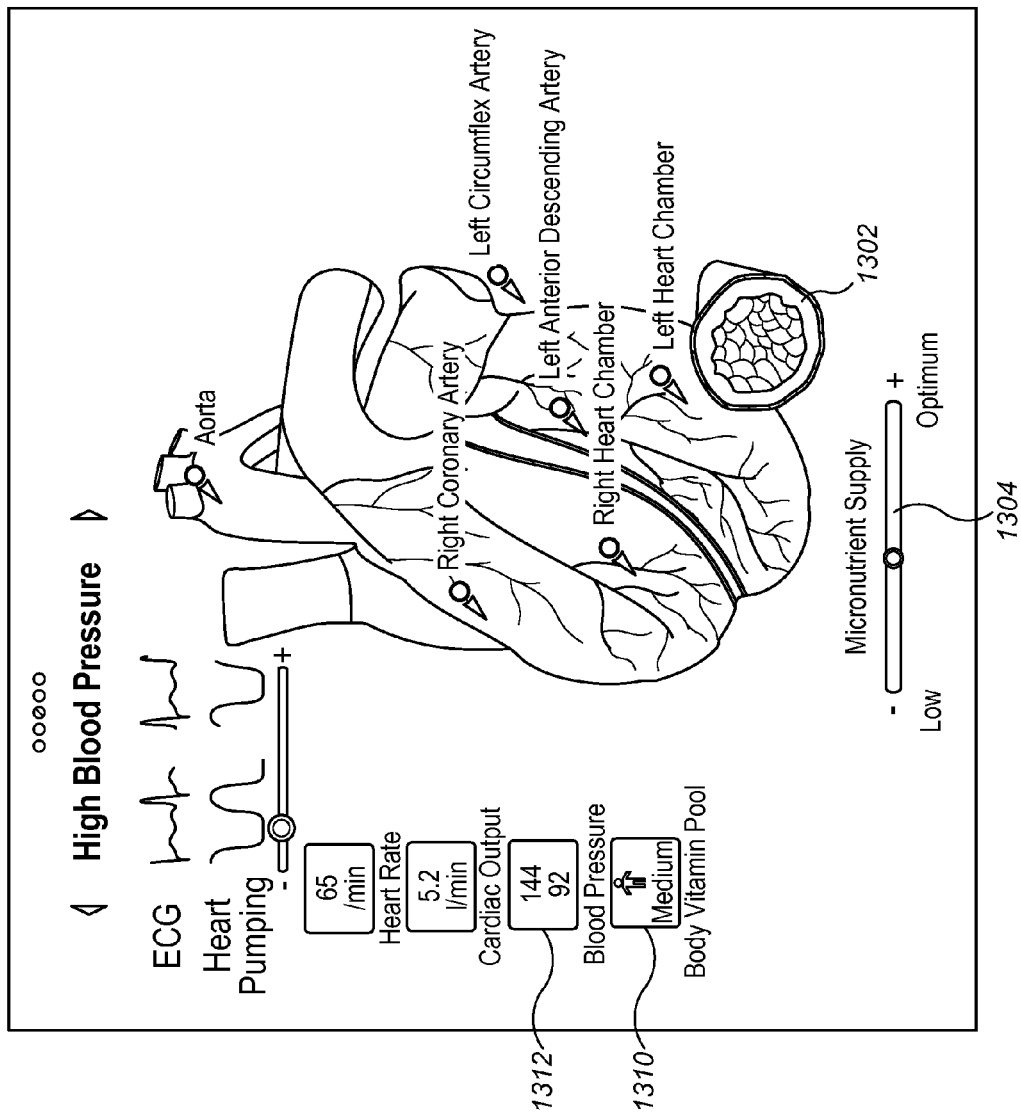
FIG. 13 is an example view of a high blood pressure model to show the effect of below requirement nutrient level at an organ level, according to one embodiment.

FIG. 13 shows effect of the micronutrient slider 1304 in middle position and its effect on arterial wall 1302, blood pressure 1312, and body nutrient pool 1310. This graphical user interface may also has certified medicine prompter that may prompt you for taking prescribed medicine on a timely basis and the cellular medicine box for being prompted to take a particular type of micronutrient that is optimal as cellular medicine.

Figure 14:
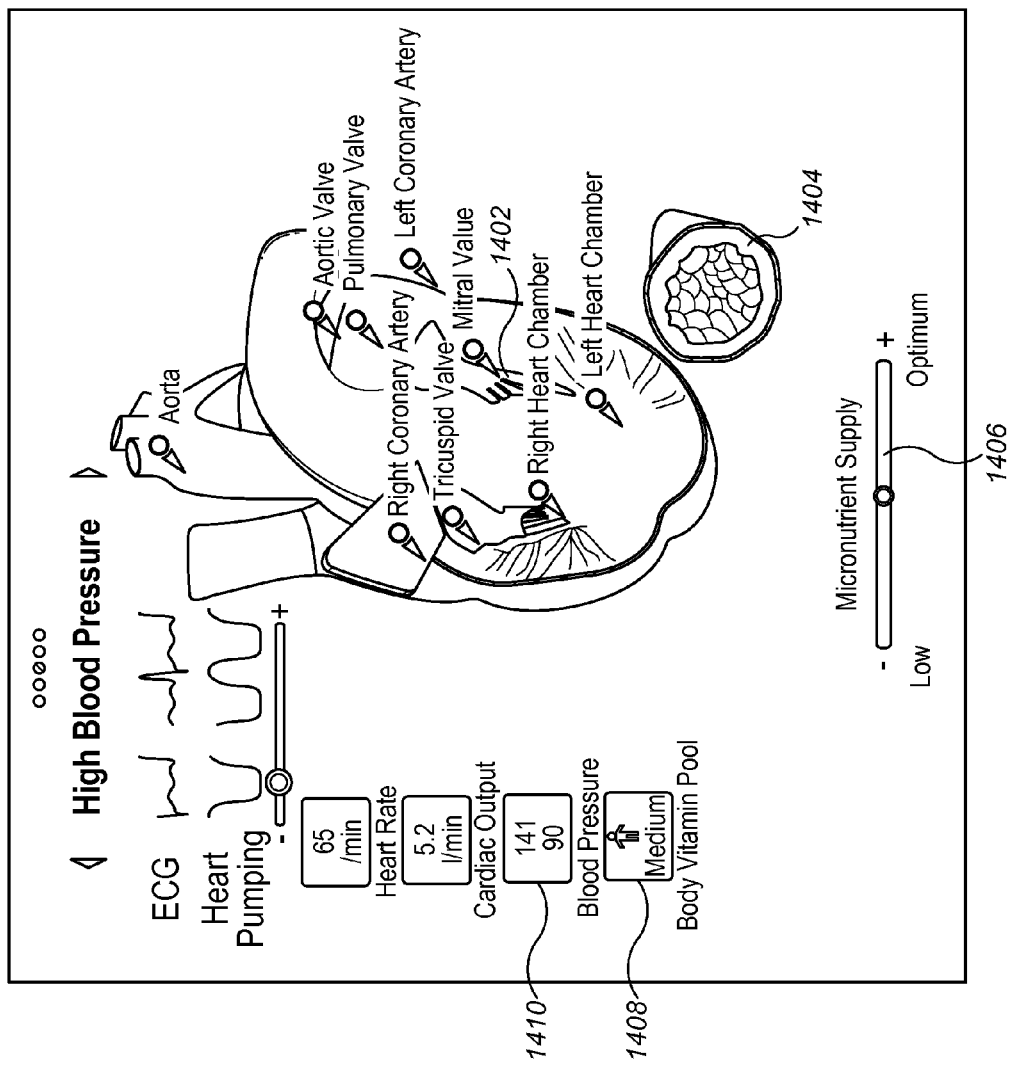
FIG. 14 is an example view of a high blood pressure model of heart tissue and artery to show the effect of below requirement nutrient level in a cross sectional heart, according to one embodiment.

FIG. 14 is a cross sectional view of the same slider position 1406 as the FIG. 13. It is showing the cross sectional heart 1402, arterial wall that is thickened 1404 and the vital signs in box 1410 and the body vitamin pool 1408.

Figure 15:
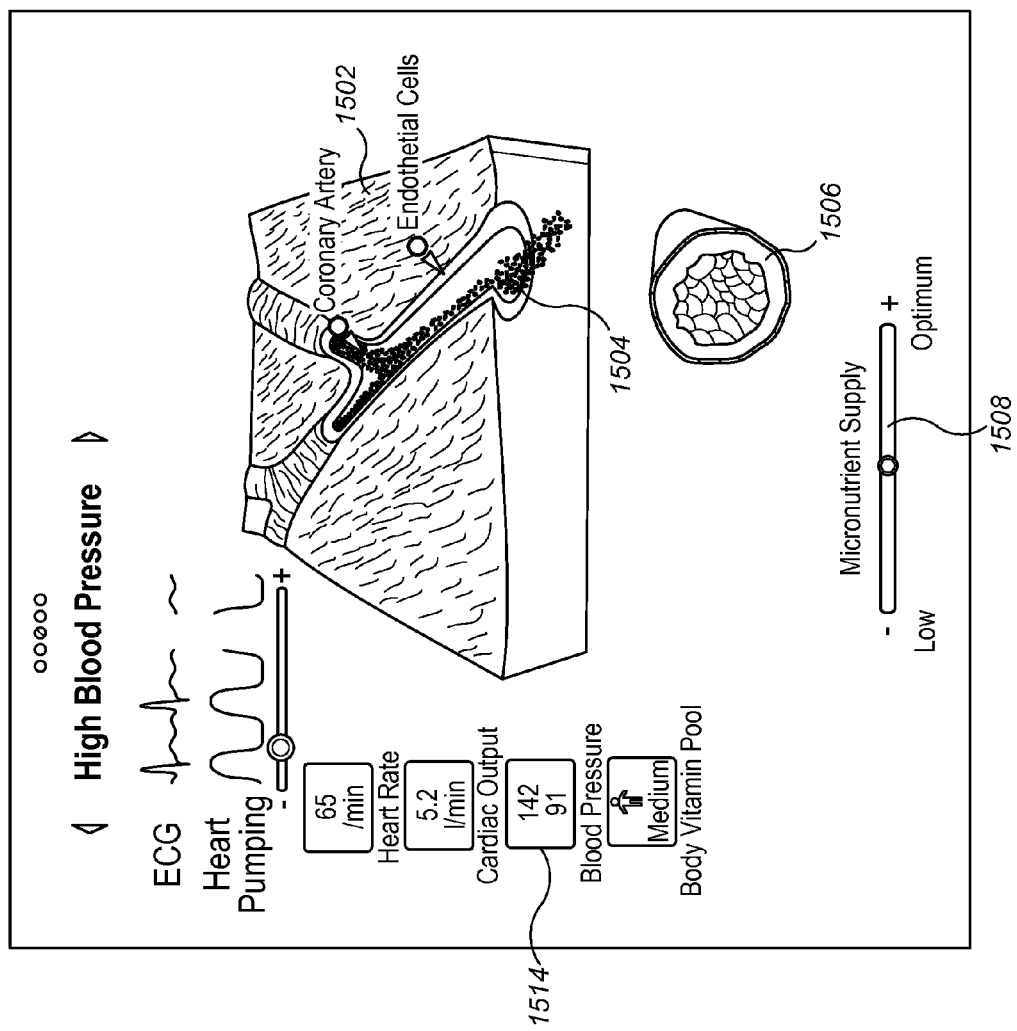
FIG. 15 is an example view of a high blood pressure model of heart tissue and artery to show the effect of below requirement nutrient level in a cross sectional heart, according to one embodiment.

FIG. 15 is a tissue view of the same slider position 1508 as the FIG. 13. It is showing the tissue 1502, micronutrient flow 1504, arterial wall that is thickened 1506 and the vital signs in box 1514. These different views show how easily one may transition from one view to another from an organ level to subcellular level with sweeping actions.

Figure 16:
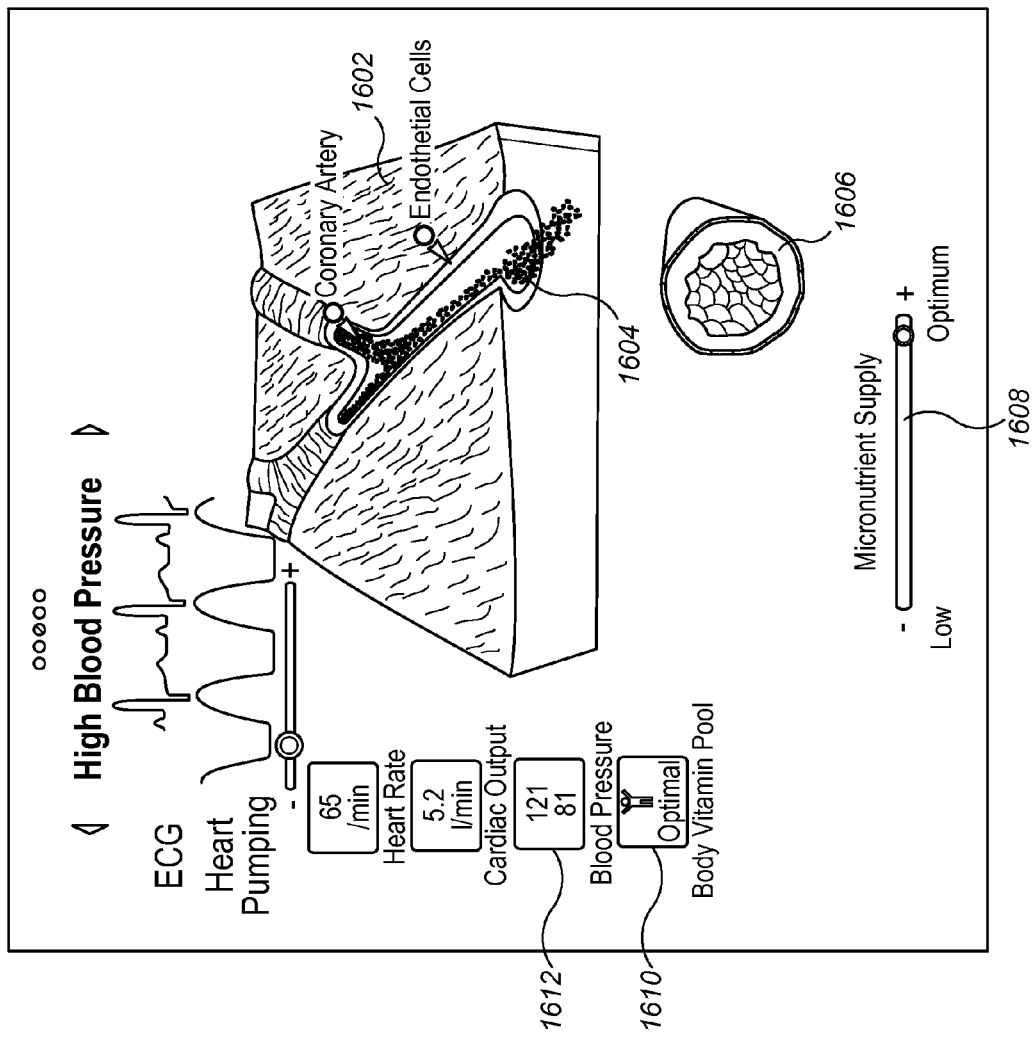
FIG. 16 is an example view of a high blood pressure model of heart tissue and artery to show the effect of sufficient nutrient level, according to one embodiment.

FIG. 16 is a tissue view of the same slider position 1608 as the FIG. 11. It is showing the tissue 1602, increased micronutrient flow 1604, arterial wall that is thinner 1606, the vital signs in box 1612 and the body vitamin pool box 1610 shows optimal level.

Figure 17:
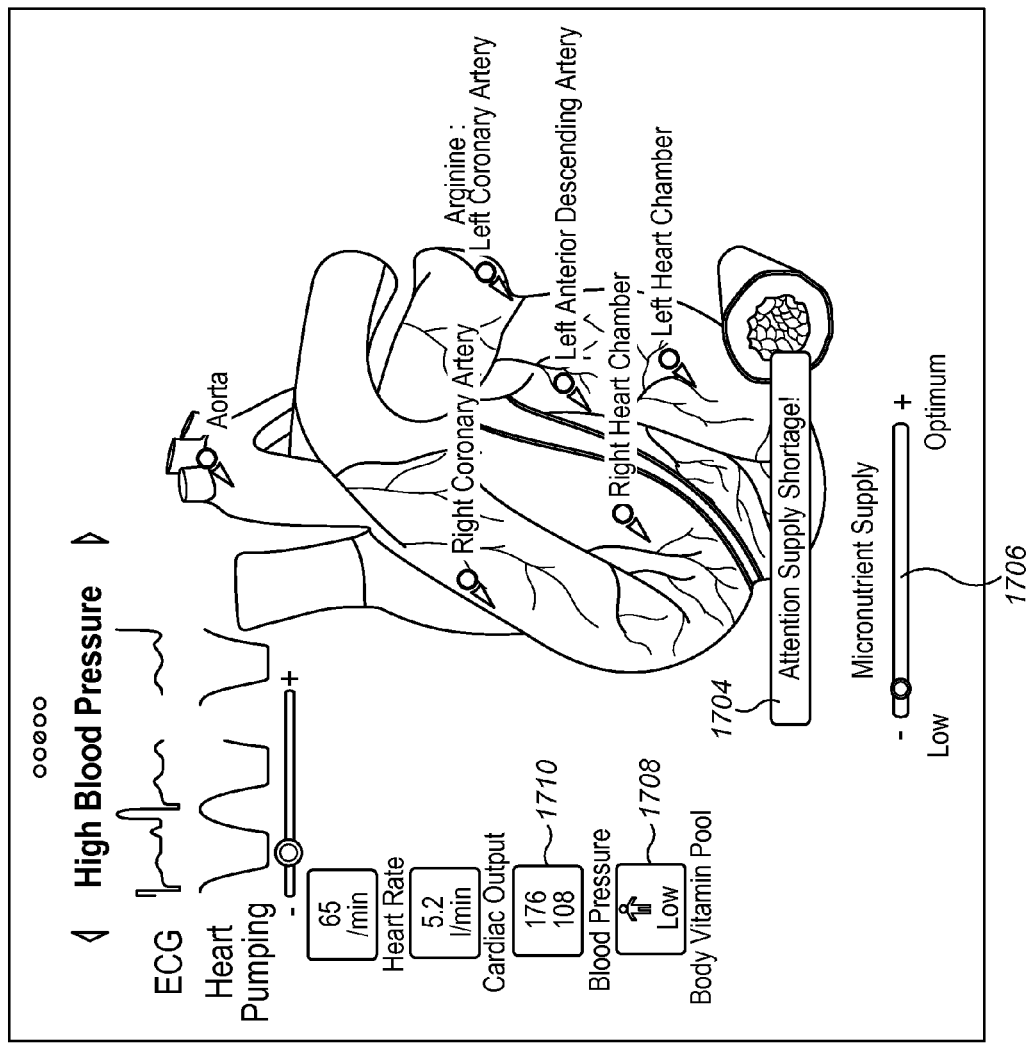
FIG. 17 illustrates the warning signs that may be displayed from high blood pressure individual regarding nutrient level, according to one embodiment.

FIG. 17 shows the slider bar 1706 at the extreme left and a message across the screen 1704 flashing "Attention Supply Shortage!". The text box that may pop up may suggest what the things that is required. The blood pressure box 1710 shows a red color increased blood pressure and the body vitamin pool box 1708 shows red. The box 1708 may also show that medication is deficient. For different diseases such as asthma etc., it may prompt to take inhalers if the lung shows it is under stress. The examples are not just limited to heart conditions it may also be for cancer, infectious diseases, metabolic diseases and others.

Figure 18:
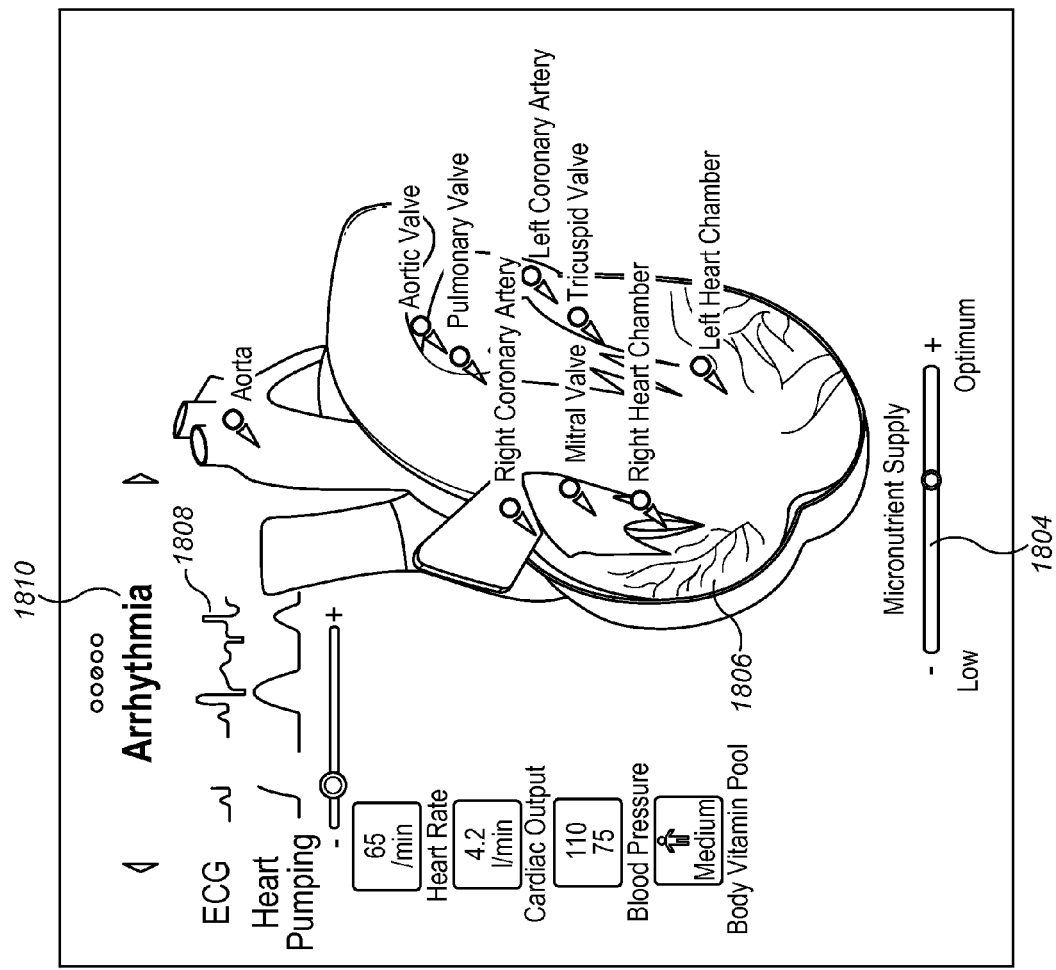
FIG. 18 illustrates a cross functional view of the heart during Arrhythmia, according to one embodiment.

Arrhythmia means ones heartbeat is irregular. It doesn't necessarily mean your heart is beating too fast or too slow. It just means it's out of its normal rhythm. It has been connected with lack of micronutrients in a study done by Blue Cross and Blue shield (2013). They have strongly suggested monitoring intracellular micronutrients levels and have approved the testing for insurance coverage and listed several vitamins and minerals to be reported. They also observed that the heart condition improves in users when they are treated with micronutrient intake (Blue Cross Blue shield Study (July 2014). This just shows that our invention of integrating data from personal medical data and alerting the user of the deficiency ahead of time prevents and cures the user who is already having heart problems. FIG. 18 shows a screen shot of the mobile device of a user who is suffering from Arrhythmia 1810. The graph 1808 shows irregular heartbeats and the electrical current inside the heart muscle also show irregularity 1806. The micronutrient supply at an increased level as shown in the slide 1804 shows that at least the heart rate and cardiac output is normal and the recommendation in the text box 1802 shows how important the micronutrient intake is.

Figure 19:
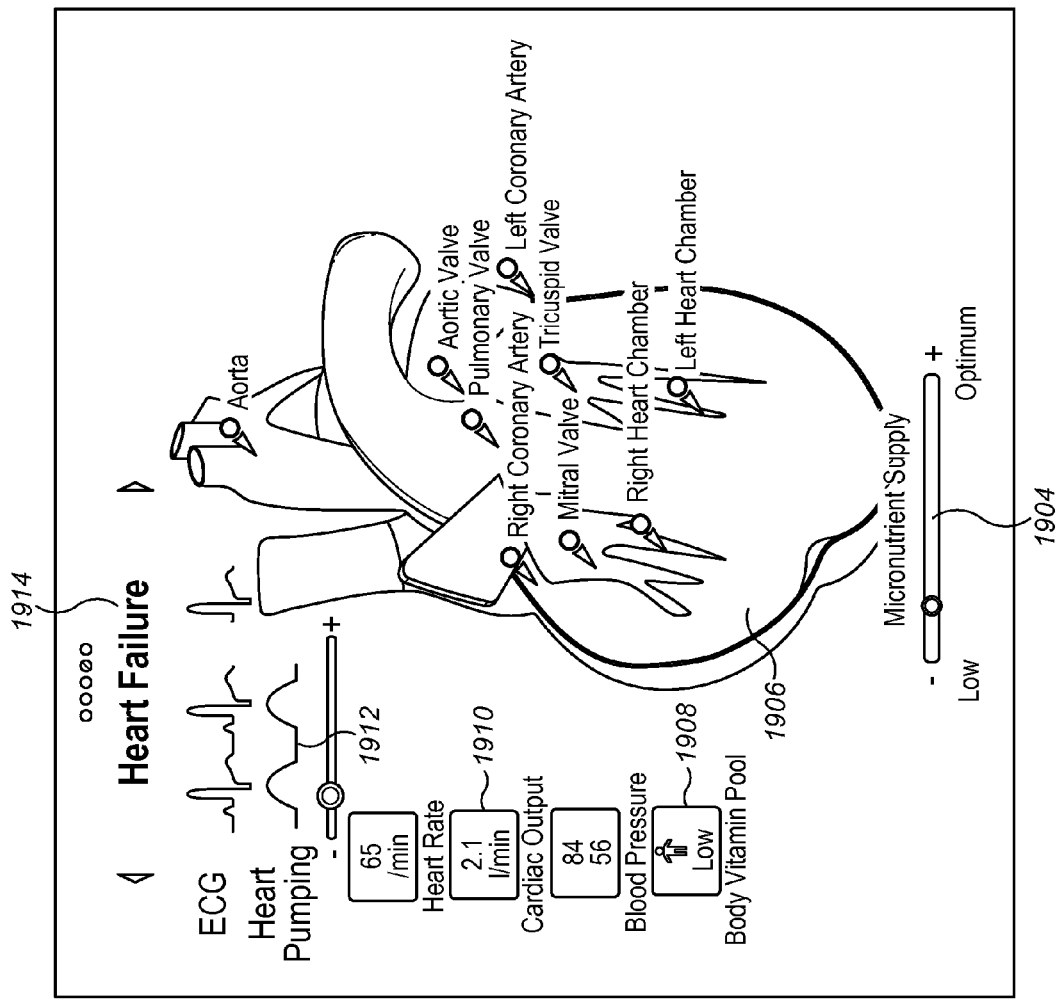
FIG. 19 illustrates a cross functional view of the heart during heart failure, according to one embodiment.

FIG. 19 shows a graphical display of the user's heart failure 1914 scenario. The pop up text box may advise and suggest the patient to do the needful before they go to the hospital. The low micronutrient or nutrient slide 1904 is indicating the level and correlating the level of macro or micro nutrient effect to that of the cross section of the heart and showing an enlarged heart 1906. The body nutrient pool 1908 is showing that there is a deficiency and an intake is necessary. The heart pumping 1912 and cardiac output 1910 is showing dangerous situations.

Figure 20:
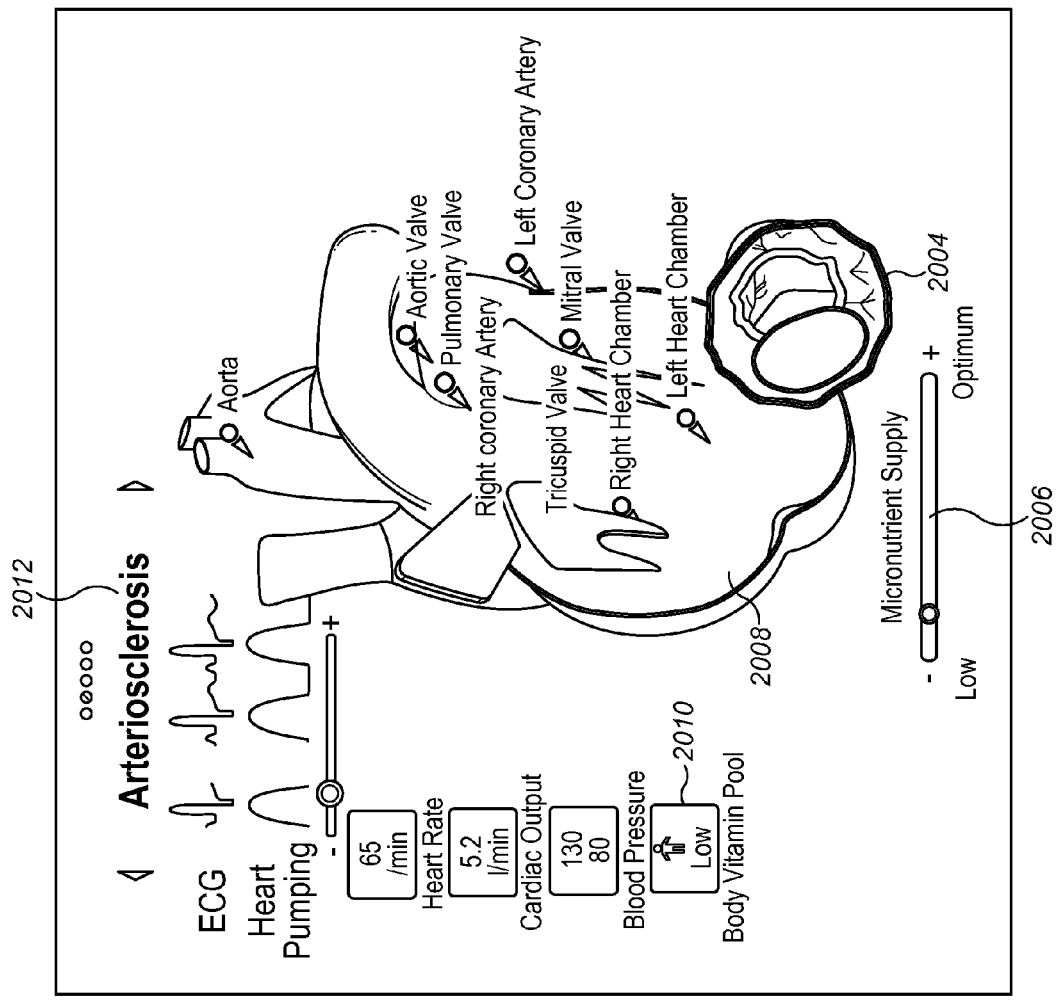
FIG. 20 illustrates a cross functional view of the heart during Arteriosclerosis, in one embodiment.

Arteriosclerosis 2012 in FIG. 20 is a disease that manifests primarily due to bad dietary habits, micronutrient deficiency and other risk factors. A clogged artery 2004 is shown in correlation to nutrient deficiency slide bar 2006. The elongated heart that is in poor condition is shown as 2008. The body micronutrient pool 2010 may be shown in red as to depict severe deficiency.

Figure 21:
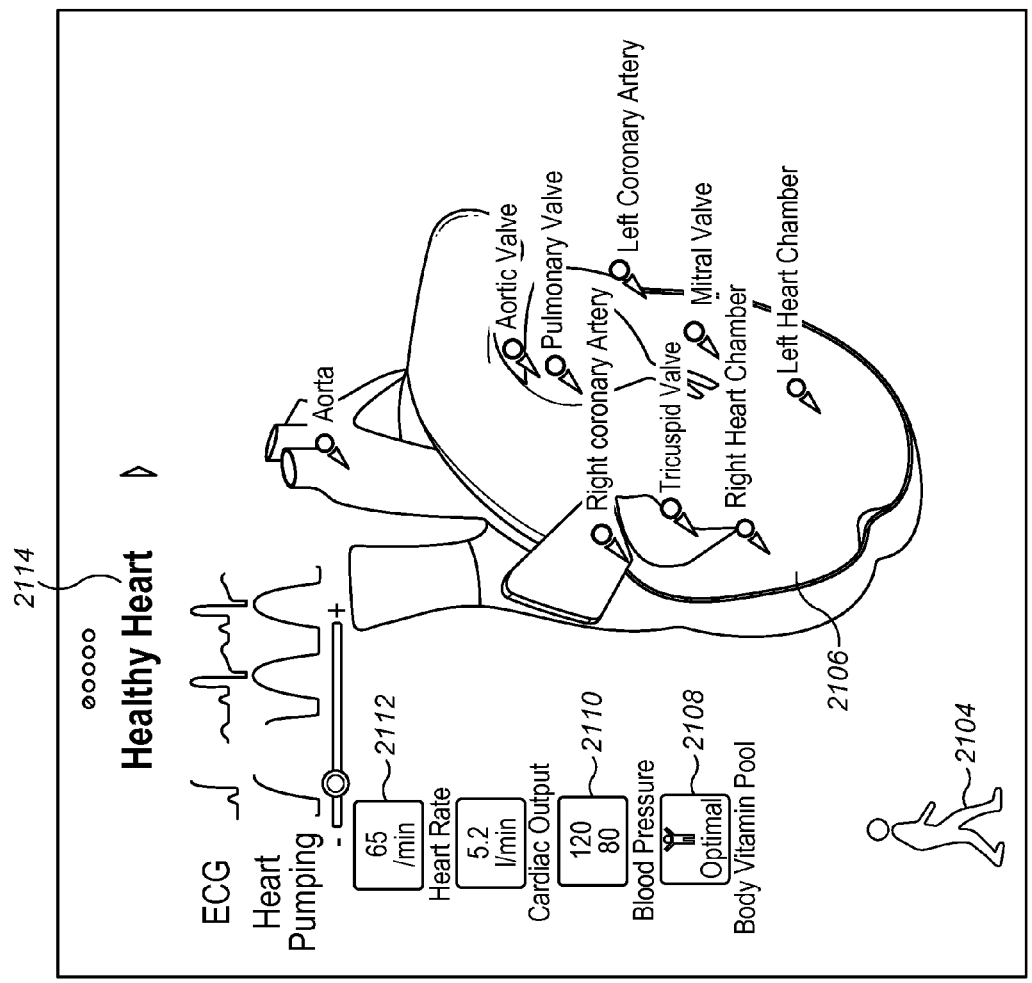
FIG. 21 shows a profile of a person's heart who has a healthy heart and is just walking, in one embodiment.
Figure 22:
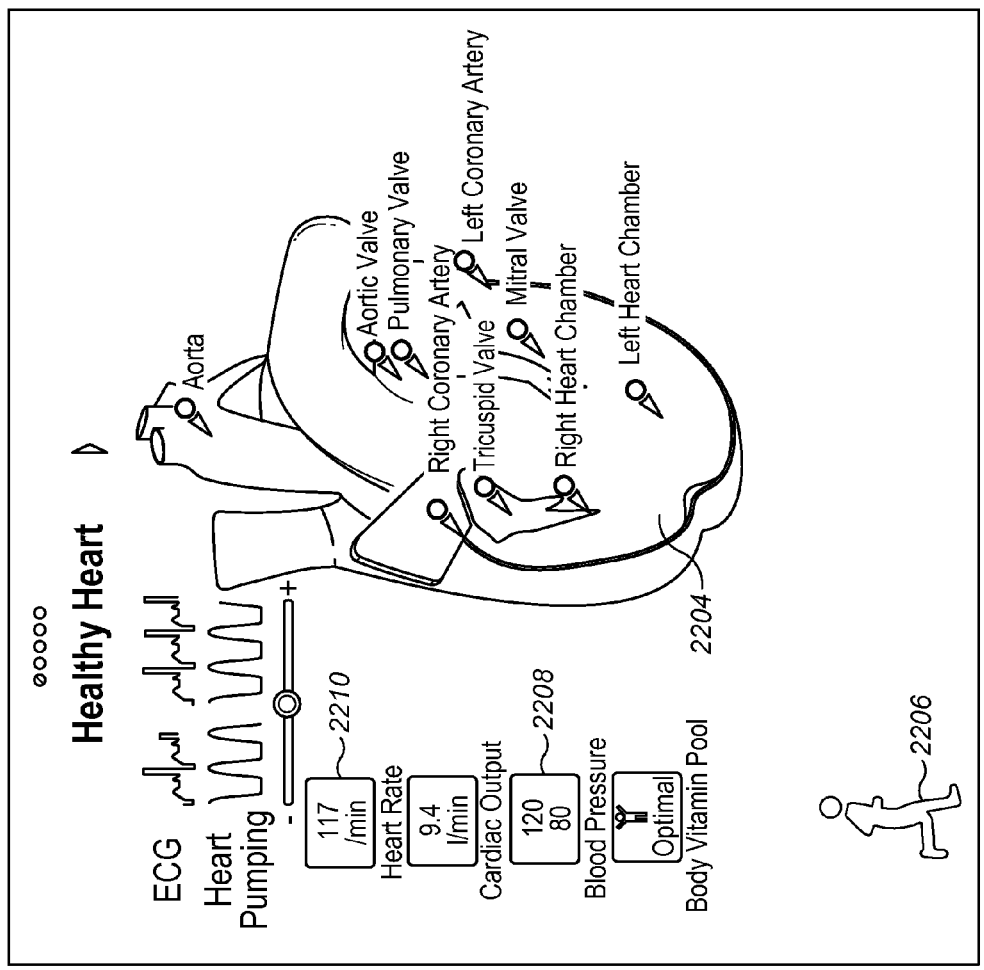
FIG. 22 shows a person running and the cross functional view of the heart and how the heart is functioning, in one embodiment.
Figure 23:
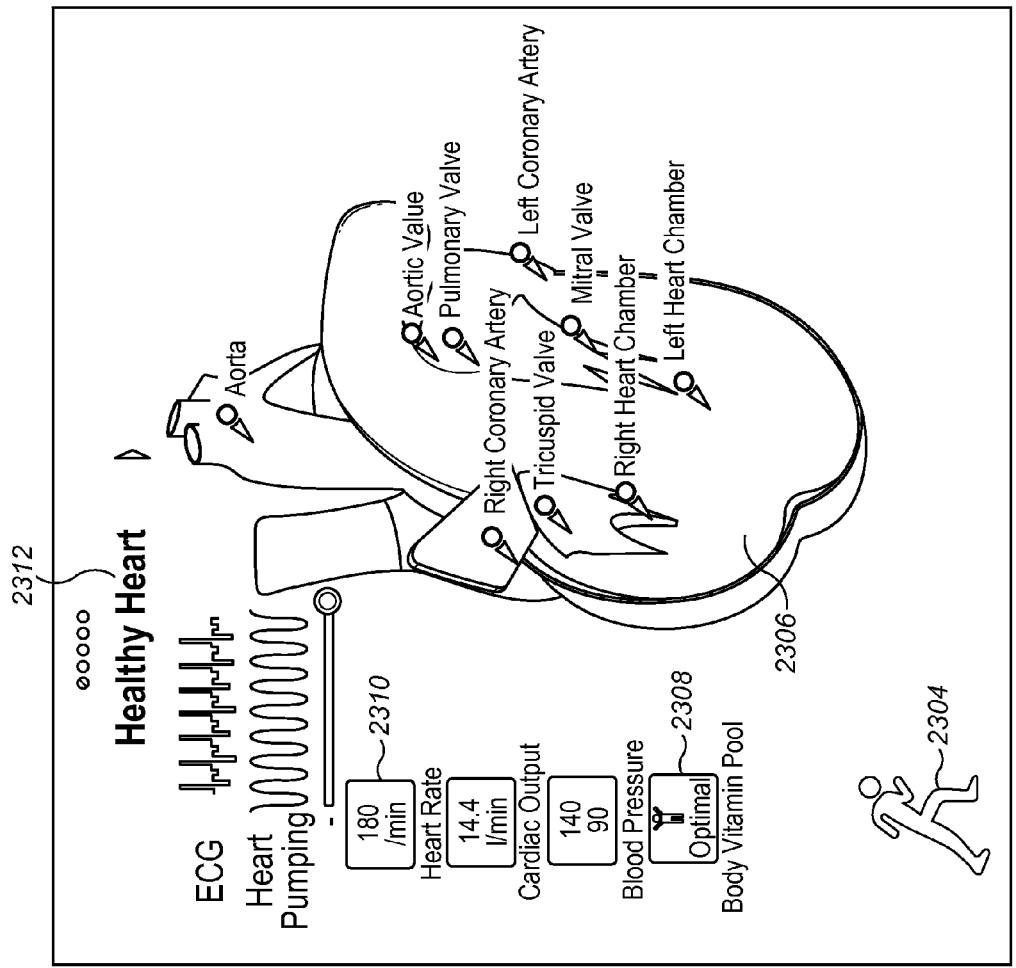
FIG. 23 shows a person running and the cross functional view of the heart with elevated blood pressure and how the heart is functioning, in one embodiment.

FIGS. 21, 22 and 23 show a normal human being doing various activities. The walking person 2104 that has a healthy heart 2114 has all his signs in 2112, 2110, 2108 in normal range. Whereas in FIG. 22 the user 2206 is jogging having a healthy heart and the parameters that are being measured and displayed are 2210 heart rate, blood pressure 2208, cross sectional heart 2204 looks normal and text pop up box may advise by displaying the nutrition updates. In FIG. 23, the same healthy heart 2312 user 2304 when starts running they show altered blood pressure and heart rate 2310 akin to normal exercise stress and showing cross sectional normal heart 2306. The micronutrient body vitamin pool 2308 shows the current level. The pop up text box may imply to take nutrients after or before the exercise to keep the heart healthy. This kind of display may be more pertinent to normal user who likes to keep an account of their dietary habits and exercise routine. The wearables and mobile devices may house this integrated real time display to encourage and archive their achievements. These displays may be displayed on every wearable in real time. The user may change different renditions of his or her's own organ, system or a particular part of the body to monitor in healthy or diseases conditions. One may also monitor other persons health condition for example a mother might like to monitor her child or a care taker their ward etc. This also may allow and display of monitoring of pharmaceutical drug therapies', 'pharmaceutical interventions' or alike.

Although the present embodiments have been described with reference to specific example embodiments, it will be evident that various modifications and changes may be made to these embodiments without departing from the broader spirit and scope of the various embodiments. For example, the various devices, modules, analyzers, generators, etc. described herein may be enabled and operated using hardware circuitry (e.g., CMOS based logic circuitry), firmware, software and/or any combination of hardware, firmware, and/or software (e.g., embodied in a machine readable medium). For example, the various electrical structure and methods may be embodied using transistors, logic gates, and electrical circuits (e.g., application specific integrated (ASIC) circuitry and/or in Digital Signal Processor (DSP) circuitry).

Figure 24:
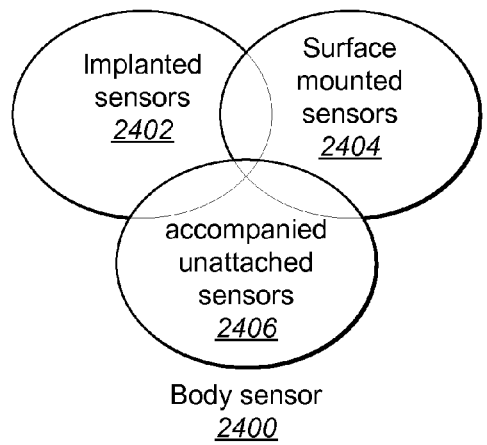
FIG. 24 shows the body sensor types that are used, namely implanted sensors, surface mounted sensors and accompanied unattached sensors.

FIG. 24 shows the types of sensors in a Body Sensor Network (BSN) 2400. BSNs have three types, namely implanted sensors 2402, Surface mounted sensors 2404 and accompanied unattached sensors 2406. Implanted sensors 2402 are generally very small in dimension, typically less that one cent coin, which are predominantly used in measuring the physiological information real-time of particular organs. For example, neuro-stimulators are implanted sensors in brain to detect neuro activities. Similarly insulin pumps, pacemakers, cochlear implants, food drop implants, gastric stimulators and glucose monitors can be implanted for measuring real time information directly from the organs.

Surface mounted sensors 2404 are those in general worn by the users either in hand, neck, chest or foot. Fitbit is a classic example of surface mounted sensor equipment that measures physical and sleep activity. Similarly, sensors worn across chest measure heart rates quite accurately. Another example of surface mounted sensor is the blood pressure cuffs worn to measure the systolic and diastolic readings. Accompanied unattached sensors 2406 are those that are not worn by the user and is either in the user's pocket or handbag. Pedometer to measure the number of steps walked is a classic example of accompanied unattached sensor 2406. Others that fall into this category are motion sensor and GPS.

Figure 25:
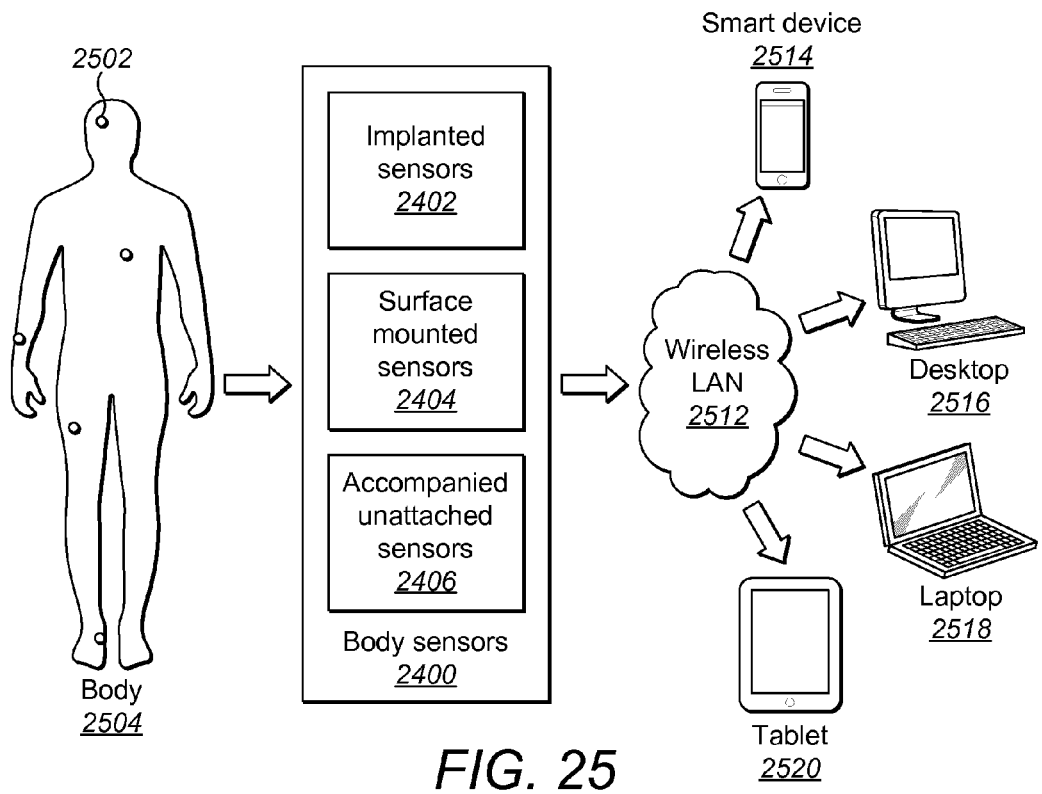
FIG. 25 shows the front end high level architecture of body sensor network.

FIG. 25 provides the front end high level architecture. Any user's body 2504 has several sensors mounted. The body sensors 2400 comprise of implanted sensors 2402, surface mounted sensors 2404 or unattached sensors 2406. For example, neuro stimulator sensor 2502 is an implanted sensor. Body sensors relay real-time information periodically to the user device over wireless medium 2512. The user device can be a smart device 2514, desktop 2516, laptop 2518 or a tablet 2520. The body sensors in this example comprises of neuro stimulators, insulin pumps, pace makers, cochlear implants, foot drop implants, mini robots injected or incorporated inside the body to monitor, delver, diagnose and treat diseases or deploy medications, gastric simulators and glucose monitors. The surface mounted sensors may comprise of blood pressure monitors, heart rate monitors, ECG, EDG and electromyography etc. The unaccompanied unattached sensors comprise of pedometer, motion sensors, electrolyte detection sensors, GPS, medical chairs, vehicle sensors that may be used to monitor the condition of the driver and report wirelessly to the service provider.

Figure 26:
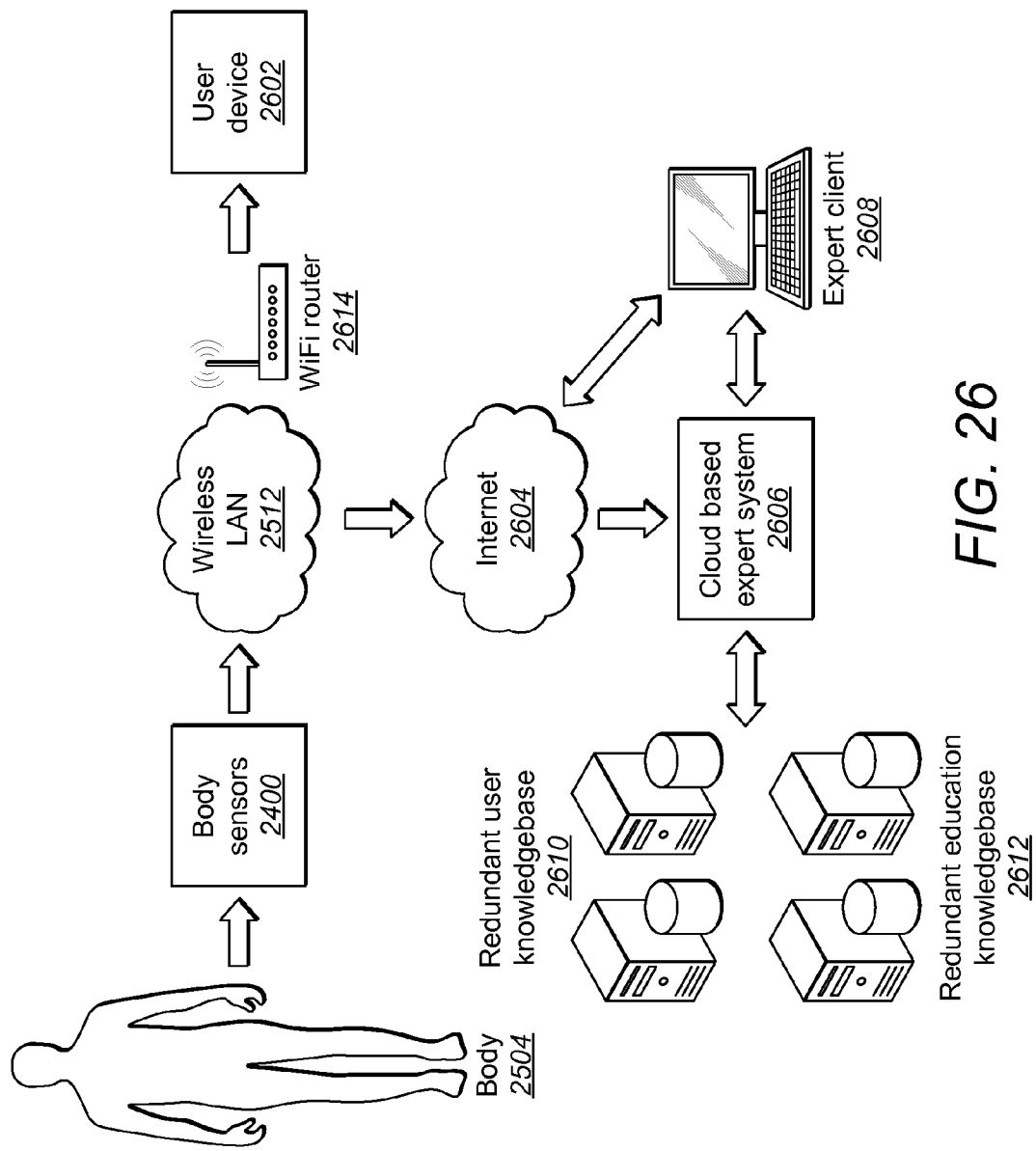
FIG. 26 shows the back end system architecture of cloud based expert system.

FIG. 26 shows the back end expert system software architecture. The sensor information collected by the user devices 2602 over wireless LAN interface 2512 from the body sensor 2400 worn or implanted in the user 2504 are stored in a local data base and is relayed over Internet 2604 to the cloud based expert system 2606. The cloud based expert system 2606 can be present anywhere in the world and not necessarily proximal to user devices. The cloud based expert system is accessed by experts to view the user details either to answer question or to analyze the sensor results through the expert client user interface 2608. The Expert Client 2608 can either be co-located with cloud based expert system 2606 or can access the expert system 2606 through Internet 2604.

The cloud based expert system 2606 stores the sensor results from the user's body sensors 2522 in the user knowledgebase 2610. The storage 2610 is redundant, with data being mirrored to provide redundancy, fault tolerance and reliability. Similarly, the education knowledgebase 2612 is also redundant to provide fault tolerance. The education knowledgebase 2612 consists of important medical information that can be mapped to user sensor inputs to provide real-time education to the user on a particular subject right at the user device 2602. Similarly, the expert 2608 can provide instant real-time analysis of the collected data directly to the user device 2602 and answer user's questions.

Figure 27:
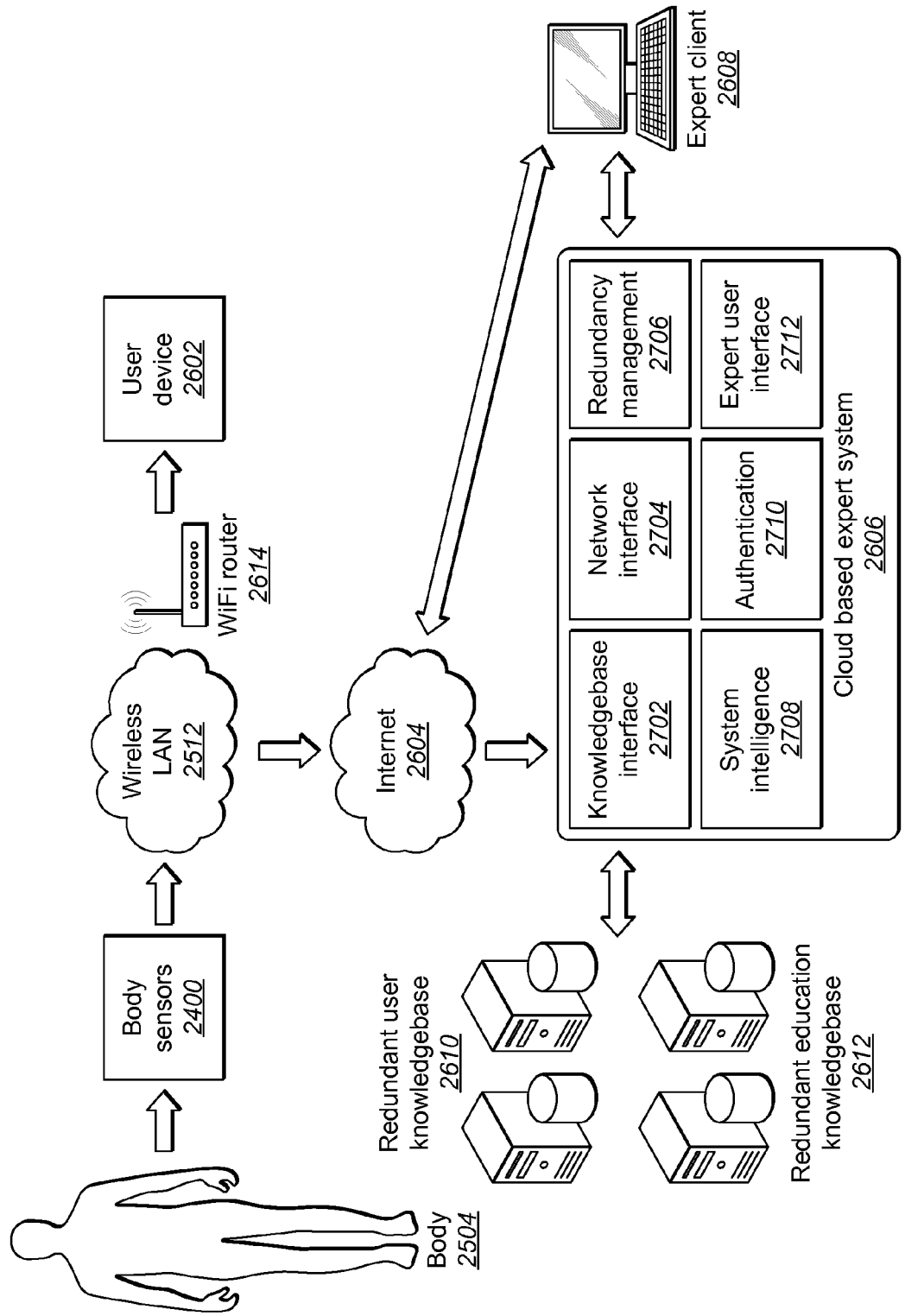
FIG. 27 shows the back end cloud based expert system software architecture.

FIG. 27 shows the back end expert system software architecture. The cloud based expert system 2606 broadly consists of six distinct modules. The knowledgebase interface 2702 provides the mechanism to interface with the redundant user 2610 and education knowledgebase 2612. The network interface 2704 handles the information transfer to and from the Internet. All sensor data and expert data that are communicated to body sensor 2400 and user devices 2602 are done through the Internet 2604 managed in the cloud based expert system 2606 by the network interface 2704. Redundancy management 2706 module is responsible for managing the user knowledgebase 2610 and education knowledgebase 2612 redundancies. The module 2706 monitors the knowledgebase constantly, handles mirroring, consistency, and data consistency. The module 2706 also handles the detection of fault, fault recovery, switch over and maintenance tasks to make sure the knowledgebase is consistent and highly available at all times.

Expert user interface 2712 manages the expert client 2608 connectivity to the expert system 2606. The connectivity can be direct or through Internet 2604. The interface 2712 provides the username and password verification, where the interface module 2712 interacts with Authentication 2710 to validate the expert logging in. In addition, the user interface handles the graphical platform for the experts to access, analyze and operate expert system 2606.

The Authentication module 2710 handles the security aspect of the expert system 2606 where it validates any login to the expert system for analyzing or communicating with either users or sensors. The authentication module handles the user validation portion of password, number of attempts allowed, password recovery, user verification to reset password and the setup of new user and password. Finally the system intelligence 2708 function is the main engine that provides the education intelligence 2802 and computation mechanism 2812.

Figure 28:
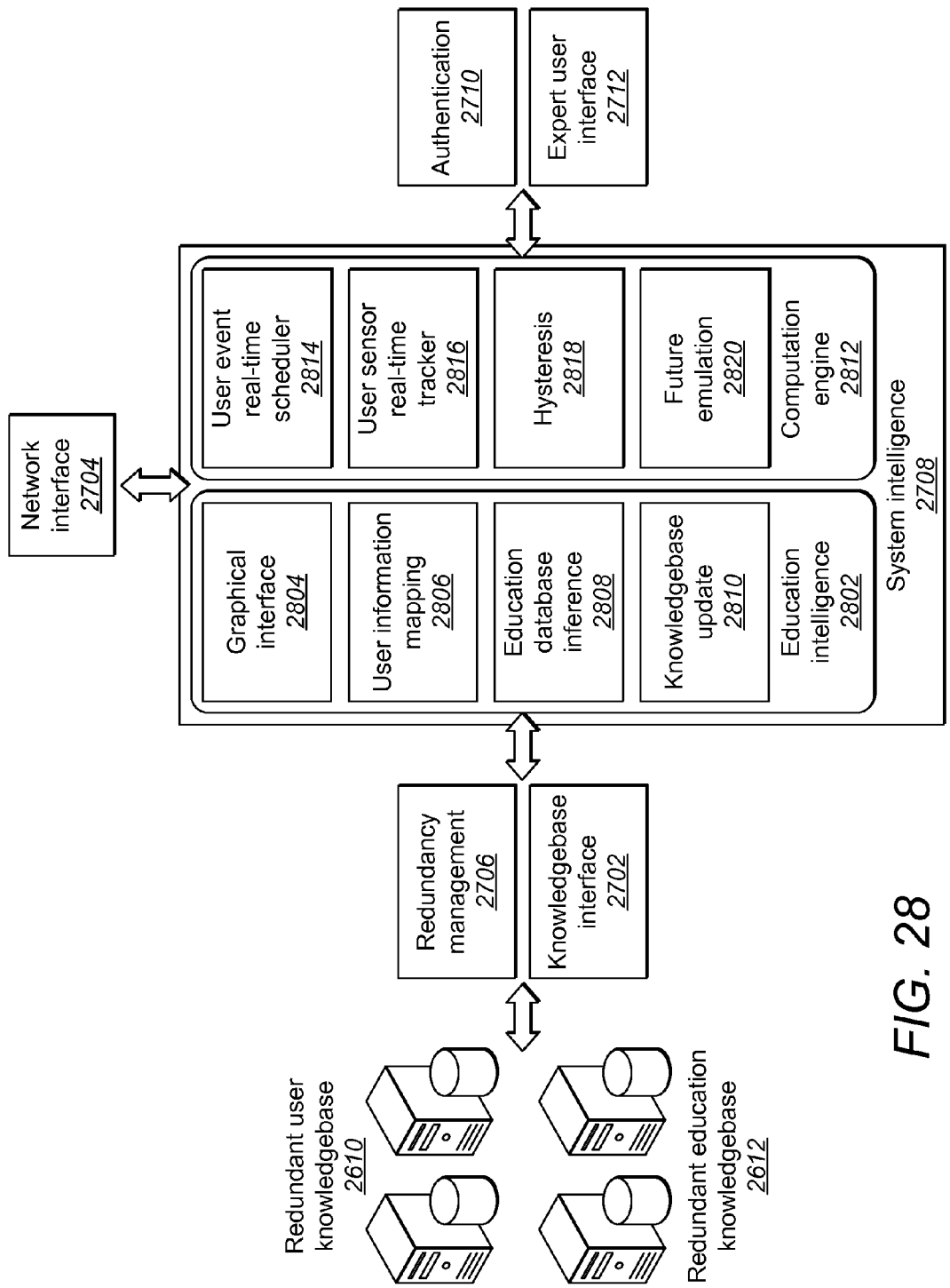
FIG. 28 shows the system intelligence module components and dependencies within the cloud based expert system module.

FIG. 28 shows the system intelligence module 2708 function in detail. The system intelligence 2708 interfaces with redundancy management 2706 and knowledgebase interface 2702 to communicate with the redundant user knowledgebase 2610 and education knowledgebase 2612. The system intelligence 2708 communicates to user and sensors over Internet 2604 through the network interface 2704. In addition, system intelligence 2708 interfaces with experts through authentication module 2710 and expert user interface 2712.

System intelligence 2708 has eight major functions to provide useful analytical results using artificial intelligence techniques. Graphical interface 2804 provides the graphical user interface back end support to the experts and the user. The interface 2804 manages both data visualization, representation and animation portion of the architecture. User event real-time scheduler 2814 module is crucial as it handles the heartbeat of the system. The schedule 2814 collects data periodically from all sensors of all users real-time. The sensors are synchronized with user devices and system intelligence so the latest sensor data is available at all time. User sensor real-time tracker 2816 handles the sensor data tracking portion and the fault tolerance aspect of missing a few sensor data. The data is filled through interpolation and other numerical analysis techniques. Tracker 2816 module ensures the completeness of the data to be sent to the user knowledgebase 2610 through knowledge interface 2707.

Hysteresis 2818 module operates on the data that is stored in user knowledgebase 2610 and the new data obtained to analyze the trend and metrics that is most useful for the user. For example, an expert might analyze Body Mass Index or other complicated scenarios based on hysteresis. Future emulation 2820 module uses the hysteresis 2818 results and predictive methods to generate answers to "What if" scenarios asked by users and experts. Emulation module 2820 interacts with graphical interface 2804 to provide the results in a visually pleasing form. Knowledgebase update 2810 module interfaces with Knowledge interface 2702 to update both user knowledgebase 2610 and education knowledgebase 2612. For example, journal studies, articles, major finding, analysis, results, and important data are updated periodically so the experts and users have latest information available at all time. Also, user knowledgebase 2610 are made consistent across user devices 2602 periodically by the knowledge update 2810 module.

User information mapping 2806 module takes the sensor input from a particular user and intelligently maps it to keywords and tags needed for classification in education. Education database inference 2808 module provides the intelligence needed to take the tags and keywords to identify the relevant educational portfolio in the education knowledgebase 2612 that can impact the user. For example, if the analysis finds a user's cholesterol level as high, then the education database inference engine 2808 gets impact articles based on tags produced by mapping module 2806. The tags in this case could be heart disease, heart attack, plaque, stroke, cardio exercises etc.

Figure 29:
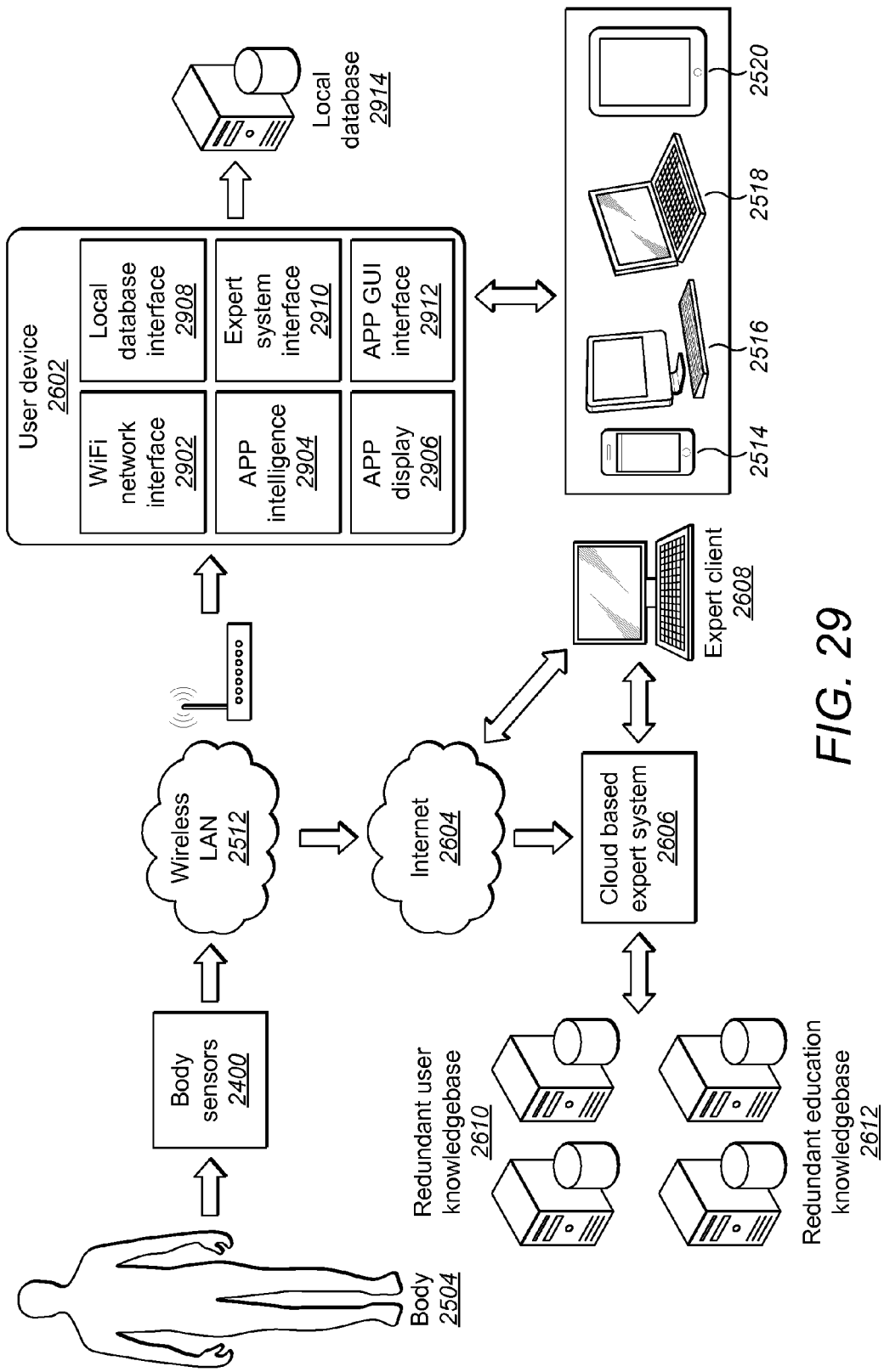
FIG. 29 shows the user device software architecture and its components.

FIG. 29 provides the user device 2602 software architecture. The software methodology consists of six methods that interface with local database 2914 that exists within the user device 2514, 2516, 2518 and 2520. The data collected in all the local databases 2914 are made consistent periodically by the cloud based expert system. WiFi network interface 2902 interfaces with the communication medium to interact with body sensors 2522 and expert system 2606. Local database interface 2908 is the main link to the local database 2914 where all the initial sensor data is collected. Expert system interface 2910 is the primary interface to communicate with expert system 2606. For example, data consistency between expert system 2606 and the user device local data base 2914 is handled by the expert system interface 2910. All communication between expert system 2606 and the expert client 2608 to the user device is interfaced through expert system interface 2910. App GUI interface 2912 provides the graphical interface to the users through which users can input data relating to health directly and also provide other important information such as user name and password. App display module 2906 handles the graphical display portion that handles the visualization in the smart device, interaction with experts, analytical graphs for present, "What if" scenarios and future emulations. App intelligence 2904 handles the overall intelligence of the body sensor network application in the user device.

Figure 30:
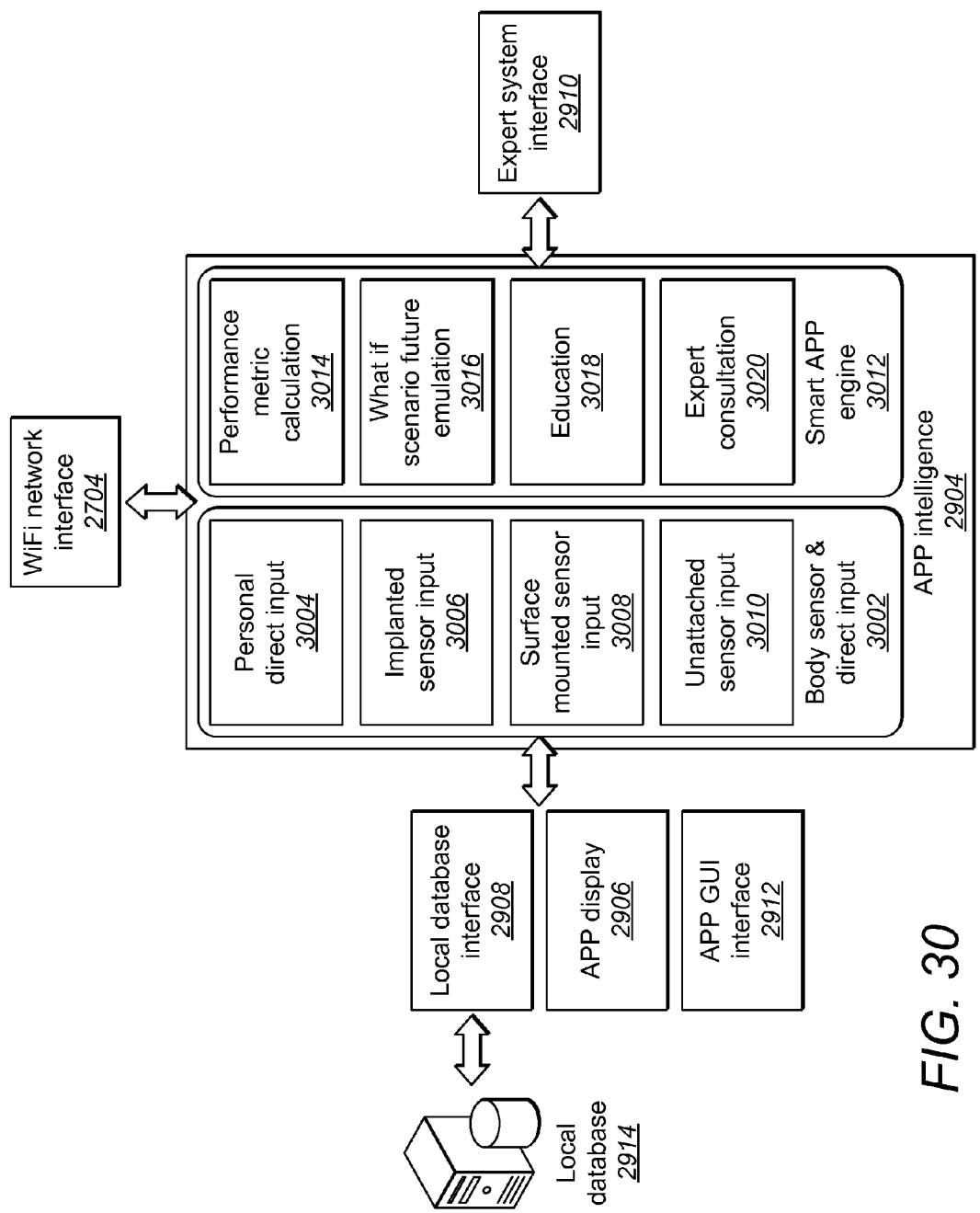
FIG. 30 shows the user device App intelligence component and its dependencies.

FIG. 30 expands the functionality of App intelligence 2904 method. App intelligence 2904 interfaces with the local database 2914 through the local data base interface 2908. It also interfaces with the users through App display 2906 and App GUI interface 2912. It communicates to the body sensors 2522 and expert client 2608 over WiFi network interface 2902. It communicates with the expert system 2606 through expert system interface 2910.

App intelligence 2904 consists of two functions. Body sensor and direct input 3002 provides the sensor input from implanted sensor 3006, surface mounted sensors such as Fit bit 3008 and unattached sensors such as Pedometer 3010. In addition, through GUI interface 2912, input directly from the user can be obtained 3004. This includes data regarding what the user consumed that day and hour. The second function is the Smart App engine 3012. This engine 3012 consists of expert consultation module 3020 that interfaces directly to the experts, who provide direct input to the user queries, provide analysis, guidance, and answers. Education 3018 module interfaces with expert system 2606 and provides important visualization information on context sensitive matter based on sensor results. "What if" scenario future emulation module 3016 interfaces with expert system 2606 and provides analytical results through visualization on the different effects based on assumptions, input and sensor values. Finally Performance metric calculation 3014 provides the graphical and tabular results of the metrics that are being tracked for the wellbeing of the user. This could be a simple height, weight, BMI graphs or a complicated blood work result graph.

Figure 31:
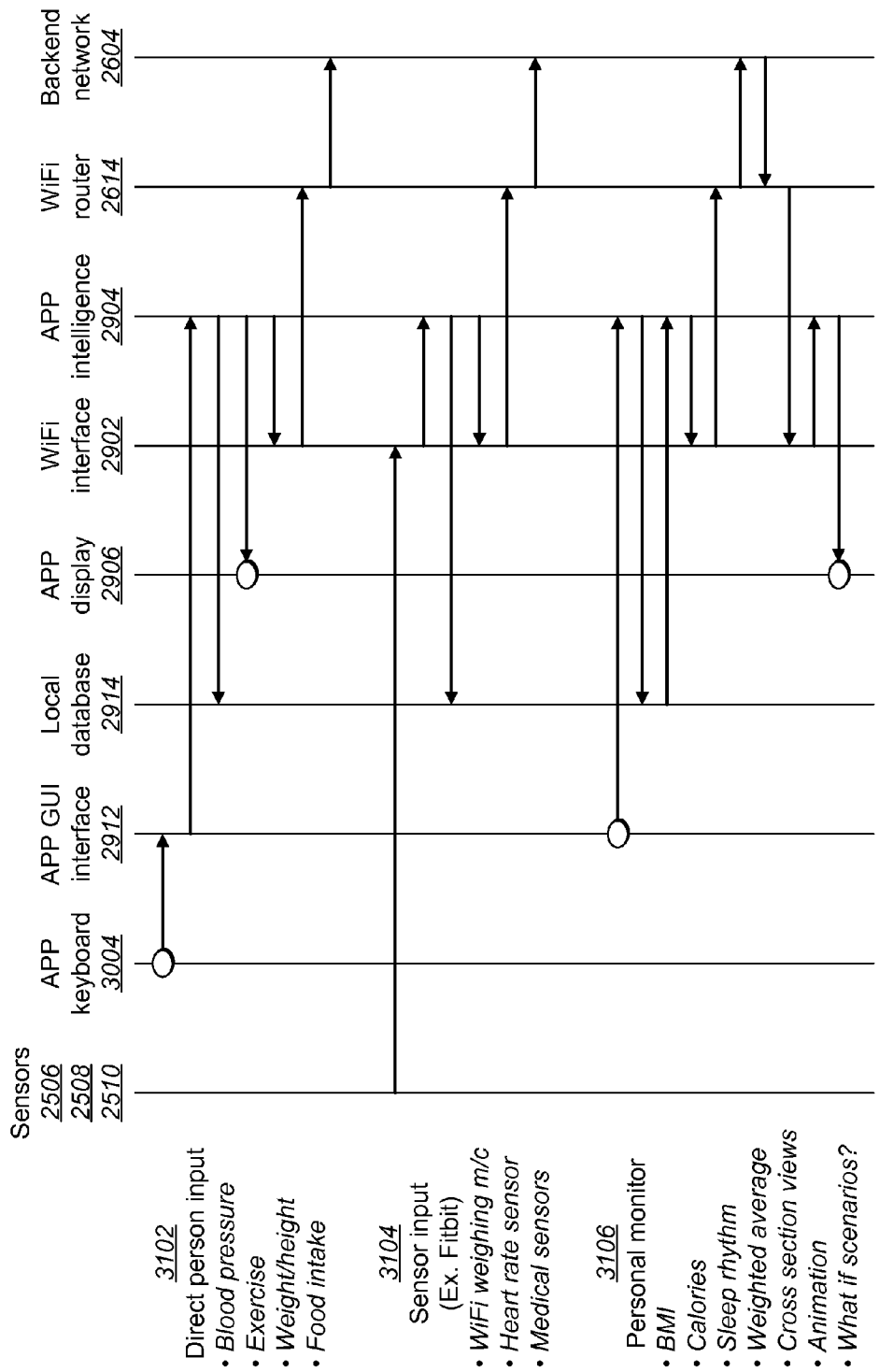
FIG. 31 shows the message sequence of user input and monitor mechanism for direct and sensory inputs.

FIG. 31 provides the message sequence chart for the user input and monitor mechanism. It shows the dependency between various modules in user device 2602. For direct person input 3102, it can be seen the user input information 3004 through graphic interface 2912 that is sent to the App intelligence 2904, which after updating sends to the local database 2914 for update and in parallel displays to the user 2906. The App intelligence 2904 also updates the information in expert system 2606 through WiFi interface 2902, WiFi router 2614 and backend network 2604.

FIG. 31 also shows sensor input 3104 message sequence, where sensors 2506, 2508, 2510 directly input values through WiFi 2902 to App intelligence 2904. App intelligence 2904 updates local database 2914, and in parallel updates information to the backend network 2604.

FIG. 31 also shows a user personally monitoring the results 3106, where the user request is made through App GUI interface 2912, which is handled by App intelligence 2904, goes through back end network 2604 to expert system 2606 and expert client 2608. The query for analysis, "What if" scenario and expert answers are received back from the expert system 2606 through backend network 2604 to the App intelligence 2904, which in turn provides the results to the user through App display 2906.

Figure 32:
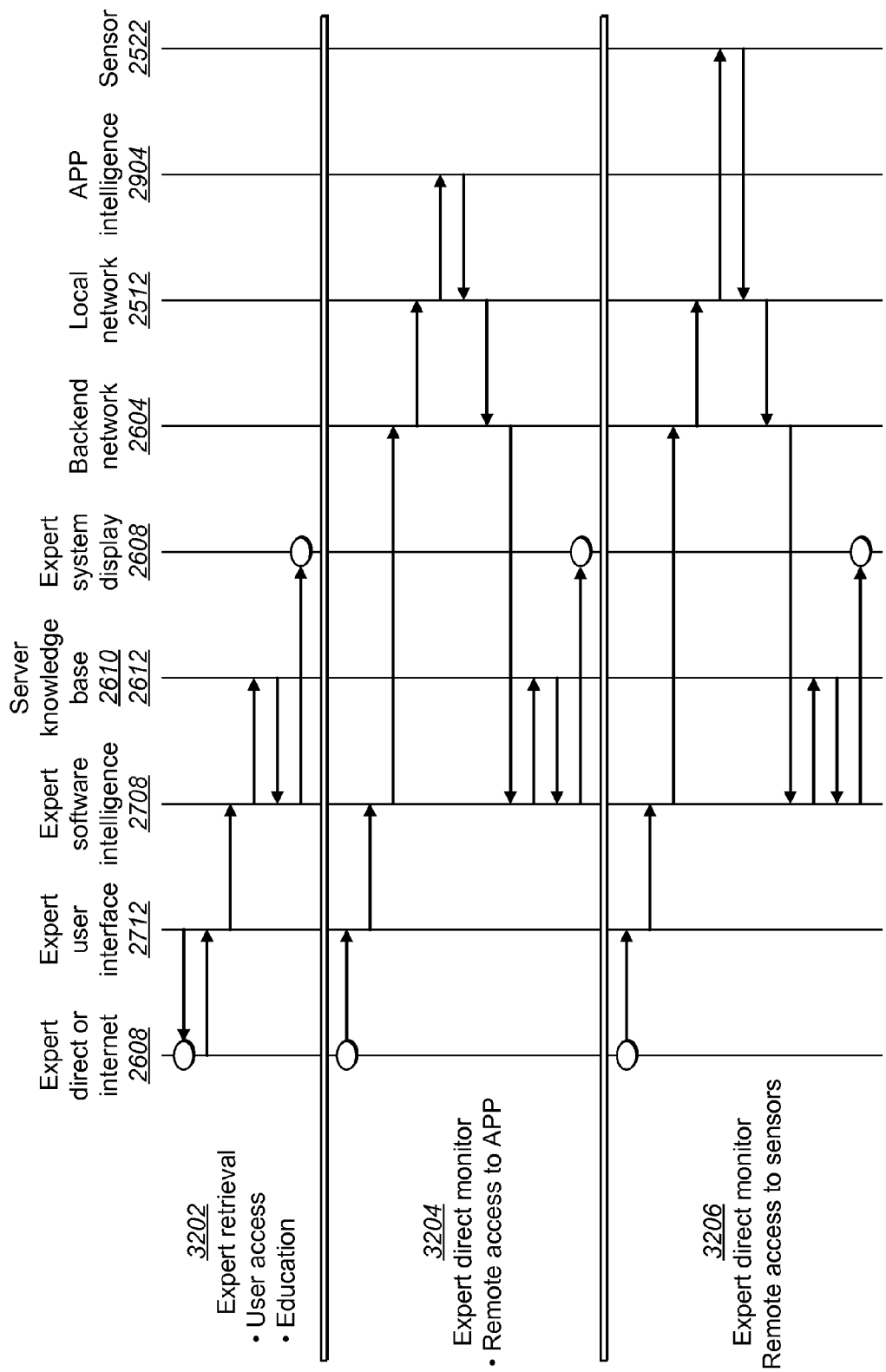
FIG. 32 shows the message sequence of retrieval mechanism by experts connected to the cloud based expert system.

FIG. 32 provides the message sequence chart for expert retrieval mechanisms. It shows the dependency between various modules in the expert system 2606. For expert retrieval of user access and education information 3203, the expert client initiates the session 2608, through user interface module 2712 communicates with system intelligence 2708. The query is handled by server intelligence 2708 accessing the knowledgebase 2610 and 2612 depending on whether it is user related or education related and displayed back to the expert client through display 2608.

FIG. 32 also shows the message sequence when an expert client 2608 directly accesses the user device 2602. The expert client 2608 through user interface 2712 places the request, which is handled by the system intelligence 2708. The communication is done through backend network 2604 and local network 2512 to reach App intelligence 2904 to contact the application user. Updates to the local database or showing education material in GUI is done by communicating the server knowledgebase 2610 and 2612 validated by expert client through display 2608. FIG. 32 also shows the expert directly monitoring sensors where possible 3206. The communication is similar to the Expert monitoring of user device 2602 except the communication is to the sensor.

This system and method described above is a seamless integration of visual display in 3D for not only the personal organ, cell or subcellular level for a given user but also based on the body sensor data the real time display of individual's own organ and connecting with his medical data to inform, calculate and emulate "what if" scenarios is the novel for this invention. This overcomes many technical challenges such as gathering data from disparate sources, using knowledgebase expert system to integrate various data and calculating in real time the out for the user and normalizing across devices.

In addition, it will be appreciated that the various operations, processes, devices and methods disclosed herein may be embodied in a machine-readable medium and/or a machine accessible medium compatible with a data processing system (e.g., a computer system), and may be performed in any order (e.g., including using means for achieving the various operations). Accordingly, the specification and drawings are to be regarded in an illustrative rather than a restrictive sense.

What is claimed is:

1. A method, comprising:
    gathering at least one of a physiological parameter, pathological parameter and therapeutic parameter automatically from a user to present for a personalized interactive display for the user on a mobile device;
    rendering at least one of a personalized reformatable physiological model and pathological model at the level of an organ, a cross section of an organ, parts of an organ, the cellular level of an organ and the subcellular level of said organ on the device;
    switching from one level to another on that visual device by performing a swiping action on a screen of the device, wherein the level is at least one of an organ to cell, cell to subcellular, subcellular to cell and cell to organ;
    dynamically updating a relevant data pertaining to a normal, disease and treatment option; and
    recording a variable in the user health for a data storage purpose.

2. The method of claim 1, further comprising:
    modifying at least one of the physiological parameter, pathological parameter and therapeutic parameter on the screen of the device and changing the rendition of the organ and the cellular level to show the effect.

3. The method of claim 2, further comprising:
    displaying a solution for the change in condition of the organ and the cellular level of said organ due to the change in parameter.

4. The method of claim 3, further comprising:
    alerting the user about the compliance of the individual therapeutic treatment.

5. The method of claim 3, further comprising:
    connecting a vendor and a service provider to the user for providing service.

6. A system, comprising:
    a device to gather body sensor data for an user using various network connections;
    a knowledgebase expert system to gather and analyze the body sensor data and a user input data;
    a screen control module to render at least one of a personalized reformatable physiological model and pathological model at the level of an organ, a cross section of an organ, parts of an organ, the cellular level of an organ and the subcellular level of said organ on the device; and
    a display control module to display a user query in a uniform manner across all the devices that the user is using.

7. The system of claim 6, further comprising:
    a device module to normalize a device data across all user device, databases and knowledgebase of expert system.

8. The system of claim 7, further comprising:
    a cloud based expert system provides real time emulation of scenarios and displays through graphical and animation medium directly into user devices.

9. The system of claim 8, further comprising:
    a cloud based expert system in the back end to handle redundancy of user sensor knowledgebase data and education information.

10. The system of claim 6, further comprising:
    an user interface to access a sensor result through a visualization module to display metrics and performance for the user.

* * * * *